US007838016B2

(12) United States Patent
Ravichandran et al.

(10) Patent No.: US 7,838,016 B2
(45) Date of Patent: Nov. 23, 2010

(54) ***VIBRIO CHOLERAE* STRAINS VCUSM1 AND VCUSM4, METHOD OF PRODUCING SAME, AND VACCINE DERIVATIVES THEREOF**

(75) Inventors: Manickam Ravichandran, Kelantan (MY); Syed Atif Ali, Kelantan (MY); Nur Haslindawaty Abdul Rashid, Kelantan (MY); Lalitha Pattabiraman, Kelantan (MY); Zainul Fadziruddin Zainuddin, Kelantan (MY)

(73) Assignee: Universiti Sains Malaysia, USM (MY)

( * ) Notice: Subject to any disclaimer, the term of this patent is extended or adjusted under 35 U.S.C. 154(b) by 569 days.

(21) Appl. No.: 11/753,311

(22) Filed: May 24, 2007

(65) Prior Publication Data

US 2008/0107691 A1 May 8, 2008

Related U.S. Application Data

(63) Continuation of application No. 10/981,760, filed on Nov. 5, 2004, now abandoned.

(51) Int. Cl.
*A61K 39/106* (2006.01)

(52) U.S. Cl. .................................................... 424/261.1

(58) Field of Classification Search ....................... None
See application file for complete search history.

(56) References Cited

PUBLICATIONS

Rijpkema et al.( Infection and Immunity vol. 60, No. 6,pp. 21-88-2193).*

Result 2 AF227752 sequence alignment to SEQ ID No. 1.*

Dalsgaard et al. ( Antimicrobial Agents and Chemotherapy, vol. 44, n.5, pp. 1315-1321, May 2000).*

Rijpkema et al.( Infection and Immunity vol. 60, No. 6,pp. 2188-2193, Jun. 1992 ).*

Result 2 AF227752 sequence alignment to SEQ ID No. I , Jan. 22, 2000.*

Dalsgaard et al. ( Antimicrobial Agents and Chemotherapy, vol. 44, n.5, pp. 1315-1321, May 2000).*

D.A. Sack et al., "Antibody Responses After Immunization With Killed Oral Cholera Vaccines During The 1985 Vaccine Field Trial in Bangladesh," The Journal of Infectious Diseases, 1991, pp. 164:407-11.

Talena Ledon et al., "Construction and Characterisation of O139 Cholera Vaccine Candidates," www.elsevier.com/locate/vaccine, 21 (2003), pp. 1282-1291.

R. Germanier et al., "Antigenicity of Cholorea Toxoid In Humans," The Journal of Infectious Diseases, vol. 135, No. 4, Apr. 1977.

M. J. Angelichio et al., "*Vibrio cholerae* Intestinal Population Dynamics In The Suckling Mouse Model of Infection", Infection and Immunity, Aug. 1999, vol. 67, p. 3733-3739.

S. R. Attridge et al., "Sensitive Microplate Assay for Detection of Bactericidal Antibodies to *Vibrio chloerae* 0139", Clin. Diagn. Lab Immunol., vol. 9, pp. 383-387, Mar. 2002.

V. P. Bondre, et al., Evaluation of Different Subcellular Fractions of *Vibrio cholerae* 0139 In Protection to Challenge In Experimental Cholera, *FEMS* Immunol. Med. Microbiol., vol. 19 (1998), pp. 323-329.

J. R. Butterton et al., "Heterologous Antigen Expression In *Vibrio cholerae* Vector Strains", Infection and Immunity, Jul. 1995, vol. 63, pp. 2689-2696.

R. A. Cash et al., "Live Oral Cholera Vaccine: Evaluation of The Clinical Effectiveness of Two Strains In Humans", Infection and Immunity, vol. 10, pp. 762-764, 1974.

J. D. Clemens et al., "B Subunit-Whole Cell and Whole Cell-Only Oral Vaccines Against Cholera: Studies on Reactogenicity and Immunogenicity," The Journal of Infectious Diseases, vol. 155, Jan. 1987, pp. 79-85.

J. D. Clemens et al., "Field Trial of Oral Cholera Vaccines In Bangladesh:Results of One-Year Follow-Up," The Journal of Infectious Diseases, vol. 158, No. 1, Jul. 1988.

S. N Cohen, et al., "Nonchromosomal Antibiotic Resistance In Bacteria: Genetic Transformation of *Escherichia coli* By R-Factor DNA", Proc. Natl. Acad. Sci. vol. 69 (8): pp. 2110-2114, Aug. 1972.

Trinka S. Coster, et al., "Safety, Immunogencity, and Efficacy of Live Attenuated *Vibrio cholerae* 0139 Vaccine Prototype," vol. 345, Apr. 15, 1995.

Stephen Cooper, "Helical Growth and The Curved Shape of *Vibrio colerae,*" FEMS Microbiology Letters, 198 (2001), pp. 123-124.

S. M. Faruque et al., "Epidemiology, Genetics, an d Ecology of Toxigenic *Vibrio cholera",* Microbiology and Molecular Biology Reviews, Dec. 1998, vol. 62, No. 4, pp. 1301-1314.

R. Germanier et al., "Preparation of A Purified Antigenic Cholera Toxoid," Infection and Immunity, Jun. 1976, vol. 13, No. 6, pp. 1692-1698.

Marianne Jertborn et al., Intestinal and Systemic Immune Responses In Humans After Oral Immunization With A Bivalent B Subunit-O1/O139 Whole Cell Cholera Vaccine, Vaccine, vol. 14, No. 15, pp. 1459-1465, 1998.

Thareerat Kalambaheti et al., "Immunogenicity and Protective Role of Three Formulations of Oral Cholera Vaccine," Vaccine, vol. 16., No. 2/3, pp. 201-207, 1998.

Myron M. Levine, et al., "Evaluation In Humans of Attenuated *Vibrio cholerae* E1 Tor Ogawa Strain Texas Star-SR As A Live Oral Vacine," Infection and Immunity, Feb. 1984, vol. 43, No. 2, pp. 515-522.

Frits R. Mooi et al., "The Evolution of Epidemic *Vibrio cholera* Strains," Trends In Microbiology, vol. 5, No. 4, Apr. 1997.

G. Balakrish Nair, et al., "New Bariants of *Vibrio cholera* O1 Biotype E1 Tor With Attributes of The Classical Biotype from Hospitlized Patients with Acute Diarrhea in Bangladesh," Journal of Clinical Microbiology, Sep. 2002, vol. 40, No. 9, pp. 3296-3299.

Vida K. Parsi,M.D., "Cholera," Elsevier Science Inc., 2001.

(Continued)

*Primary Examiner*—Robert Mondesi
*Assistant Examiner*—Khatol Shahnan-Shah
(74) *Attorney, Agent, or Firm*—Lowe Hauptman Ham & Berner LLP

(57) ABSTRACT

Metabolic auxotroph of *Vibrio cholerae* 0139 synonym Bengal which has a mutation in its hem A gene and which is not capable of synthesizing aminolevulinic acid (ALA) de novo and which is obtained from a parent strain originally isolated from a patient's coproculture having all the identifying characteristics of *Vibrio cholerae* 0139 synonym Bengal is described. In this strain the hem A gene is mutated by inserting a kanamycin resistant gene cassette. Another metabolic auxotroph of *Vibrio cholerae* 01 E1 Tor where the hem A gene is mutated by a frame shift mutation is disclosed. Methods of producing the strains are disclosed.

19 Claims, 5 Drawing Sheets

OTHER PUBLICATIONS

Nathaniel F. Pierce, et al., "Determinants of the Immunogenicity of Live Virulent and Mutant *Vibrio cholerae* O1 in Rabbit Intestine," Infection and Immunity, Feb. 1987, vol. 55, No. 2, pp. 477-481.

Edward T. Ryan, et al., "Cholera Vaccines," Clinical Infectious Diseases, 2000; vol. 31, pp. 561-565.

Joachim Reidl et al., "*Vibrio cholerae* and cholera: Out of The Water and Into The Host," FEMS Microbiology Reviews, vol. 26 (2002), pp. 125-139.

William M. Spira, et al., "Simple Adult Rabbit Model for *Vibrio cholera* and Enterotoxigenic *Esherichia coli* Diarrhea," Infection and Immunity, May 1981, vol. 32, No. 2, pp. 739-747.

David N. Taylor et al., "Safety, Immunogenicity, And Lot Stability of The Whole Cell/Recombinant B Subunit (WC/rCTB) Cholera Vaccine In Peruvian Adults And Children," Am. J. Trop. Med. Hyg., 1999, pp. 869-873..

M. Thungapathra et al., Construction of A Recombinant Live Oral Vaccine From A Non-toxigenic Strain of *Vibrio cholerae* O1 Serotype Inaba Biotype E1 Tor and Assessment of Its Reactogenicity and Immunogenicity In The Rabbit Model, Immunology Letters, vol. 68 (1999), pp. 219-227.

Edgar Valle, et al., "Construction and Characterization of A Nonproliferative E1 Tor Cholera Vaccine Candidate Derived From Strain 638," American Society for Microbiology, 2000.

D. A. Sack et al., "Antibody Responses After Immunization With Killed Oral Cholera Vaccines During the 1985 Vaccine Field Trial In Bangladesh," The Journal of Infectious Diseases, 1991, 164, pp. 407-411.

Edgar Valle, et al., "Construction and Characterization of A Nonproliferative E1 Tor Cholera Vaccine Candidate Derived From Strain 638," Infection and Immunity, Nov. 2000, pp. 6411-6418.

* cited by examiner

SEQUENCE LISTING

<160> NUMBER OF SEQ ID NOS: 12

<210> SEQ ID NO 1
<211> LENGTH: 2180
<212> TYPE: DNA
<213> ORGANISM: Vibrio cholerae

<400> SEQUENCE: 1

```
gacctgtgat gtaaaggaac aggttgagtt tggccggtga aggccacacg gttgtgccgt     60
ggatcatggg agcagcgtcc attgtgagat caccagttga atcgaggttt tattttgctg    120
gagtttaagt ttatcaggca gcggaatggg ctgatgttgc cactcaatcg cttggtaacg    180
ttggtattct acgtgccatt cctccgttga ggcgagtttg gtgagagtgg caagagtgtt    240
ttgttcattc aactcgtaat gggttgcttg ggtcggcaag cctaaaatcc aatcttcaag    300
ctgttcaacg ggaatatcta accctgttaa attgcggatc aggctttgtg catcttggtc    360
gcggtagatt tgatcatcat aagtttcgac ccgcgcacct tgttcatcga cctgtaagtt    420
cagcacggtt tgaccaagaa aattgcttaa acgcagtgag agtttttgtg ggcttttttg    480
ccattgaaag ttgaacgatt gtcgctgatc gggcgcgata tagccgagtt ttccggttaa    540
ttgataatgt tgaatttgtt ctagagtgac ttggtgtgat tgccattgaa cattgacggg    600
ttgtagcggt gcggtggcac aacctgccaa aagcaacaga ctcgccaatc ctggcagtag    660
gcgacgtacg agagcattca tagtgcgttt tttatccaaa gcgagagcga aaacgggcta    720
actatatcat tgatctcacg aactcaggaa aacaaatccg gtctgccctt tcaatcaaag    780
agggcatcaa gtaaaattcc gcctctagtc caccacacat atctgagaat cctctataga    840
tgtctttgct tgccattgga atcaatcaca atacggcgtc ggtagaattg cgggaaaaag    900
tggcgttcgg tccagagaag ctctctttgg cgctgaatca gctttccacc agttcacacg    960
ttaaaggagg cgtgatcctc tcaacgtgta accgcaccga aatttattgt gatgtgagat   1020
cagcaagtaa aaacaaagtc atcgaatggt tgtcccagtt tcaccaagtc agcttggatg   1080
agttaaaacc cagcctatac gttcatgaag agcaagccgc cattcgtcat ttgatgcgtg   1140
tcgcctgtgg tttggactct ctagtgttgg gcgagccgca gatattagga caagttaagc   1200
aagcttacgc agaggcgaga gagaatcacg ccgtcaatcc ggcgacggaa aagctgtttc   1260
aaaaggcttt ttcggtcgcg aaacgggtaa gaacagaaac cgaaatcggc ggcagcgcgg   1320
tttcggtcgc ttatgccgct tgcactttag caaaacacat ttttgaatcg ctggccgacg   1380
ctacggtact gttggtcggg gctggtgaaa ccattgaact ggtagcaaaa catttggccg   1440
gacaccactg taaacggatg atagtggcga accgcacgcg agagcgagct ttgagcttag   1500
gcgagcagtt tggcgccgac gtcatcgcat taaatgagat cccagactat ttagcgcaag   1560
cggatattgt gatcagctcg accgctagcc ctttgcccat cataggtaaa ggcatggtcg   1620
aaagtgcact aaaggcccgt cgccatcagc ctatgttgtt ggtggatatt gccgtgccac   1680
gcgatattga gccgcaggtc ggtaagctta acgatgctta tctctattcg gtcgatgact   1740
tgcagtcgat tgtcgatagc aatatcgagc agcgcaaagt ggaagcgatt caggcagaag   1800
cgattgtcag tgaagagagc gccaccttca tgagttggat gcgctcactg caagcggtgg   1860
acagtattcg tgattatcgt aagcaagcca atgaagcgcg tgaagagcta ctcaataaaa   1920
gtttgcaagc attggcagcg ggtggcgatc ctgaaaagct gctcatagaa ttaagcaaca   1980
aactgaccaa caaactaatt cacaccccaa cccgagcgct acaaaccgcg gcggaacaag   2040
```

-continued gggaaccggc taaactggcc gtgatcagac aaagtttagg tcttgacgat ctgaactaaa 2100
tctcaactta gagtttaaag aagcaactat gaaagcgtcg attttaagca agcttgaatc 2160
ccttgttgag cgctatgaag 2180

<210> SEQ ID NO 2
<211> LENGTH: 3316
<212> TYPE: DNA
<213> ORGANISM: Vibrio cholerae

<400> SEQUENCE: 2
gacctgtgat gtaaaggaac aggttgagtt tggccggtga aggccacacg gttgtgccgt 60
ggatcatggg agcagcgtcc attgtgagat caccagttga atcgaggttt tattttgctg 120
gagtttaagt ttatcaggca gcggaatggg ctgatgttgc cactcaatcg cttggtaacg 180
ttggtattct acgtgccatt cctccgttga ggcgagtttg gtgagagtgg caagagtgtt 240
ttgttcattc aactcgtaat gggttgcttg ggtcggcaag cctaaaatcc aatcttcaag 300
ctgttcaacg ggaatatcta accctgttaa attgcggatc aggctttgtg catcttggtc 360
gcggtagatt tgatcatcat aagtttcgac ccgcgcacct tgttcatcga cctgtaagtt 420
cagcacggtt tgaccaagaa aattgcttaa acgcagtgag agtttttgtg ggcttttttg 480
ccattgaaag ttgaacgatt gtcgctgatc gggcgcgata tagccgagtt ttccggttaa 540
ttgataatgt tgaatttgtt ctagagtgac ttggtgtgat tgccattgaa cattgacggg 600
ttgtagcggt gcggtggcac aacctgccaa aagcaacaga ctcgccaatc ctggcagtag 660
gcgacgtacg agagcattca tagtgcgttt tttatccaaa gcgagagcga aaacgggcta 720
actatatcat tgatctcacg aactcaggaa aacaaatccg gtctgccctt tcaatcaaag 780
agggcatcaa gtaaaattcc gcctctagtc caccacacat atctgagaat cctctataga 840
tgtctttgct tgccattgga atcaatcaca atacggcgtc ggtagaattg cgggaaaaag 900
tggcgttcgg tccagagaag ctctctttgg cgctgaatca gctttccacc agttcacacg 960
ttaaaggagg cgtgatcctc tcaacgtgta accgcaccga aatttattgt gatgtgagat 1020
cagcaagtaa aaacaaagtc atcgaatggt tgtcccagtt tcaccaagtc agcttggatg 1080
agttaaaacc cagcctatac gttcatgaag agcaagccgc cattcgtcat ttgatgcgtg 1140
tcgcctgtgg tttggactct ctagtgttgg gcgagccgca gatattagga caagttaagc 1200
aagcttacgc agaggcgaga gagaatcacg ccgtcaatcc ggcgacggaa aagctgtttc 1260
aaaaggcttt ttcggtcgcg aaacgggtaa gaacagaaac cgaaatcggc ggcagcgcgg 1320
tttcggtcgc ttatgccgct tgcactttag caaaacacat ttttgaatcg ctggccgacg 1380
ctacggtact gttggtcggg gctggtgaaa ccattgaaag cttcagggcg caagggctgc 1440
taaaggaacc ggaacacgta gaaagccagt ccgcagaaac ggtgctgacc ccggatgaat 1500
gtcagctact gggctatctg gacaagggaa aacgcaagcg caaagagaaa gcaggtagct 1560
tgcagtgggc ttacatggcg atagctagac tgggcggttt tatggacagc aagcgaaccg 1620
gaattgccag ctggggcgcc ctctggtaag gttgggaagc cctgcaaagt aaactggatg 1680
gctttcttgc cgccaaggat ctgatggcgc aggggatcaa gatctgatca agagacagga 1740
tgaggatcgt ttcgcatgat tgaacaagat ggattgcacg caggttctcc ggccgcttgg 1800
gtggagaggc tattcggcta tgactgggca caacagacaa tcggctgctc tgatgccgcc 1860
gtgttccggc tgtcagcgca ggggcgcccg gttctttttg tcaagaccga cctgtccggt 1920

-continued

```
gccctgaatg aactgcagga cgaggcagcg cggctatcgt ggctggccac gacgggcgtt   1980

ccttgcgcag ctgtgctcga cgttgtcact gaagcgggaa gggactggct gctattgggc   2040

gaagtgccgg ggcaggatct cctgtcatct cgccttgctc ctgccgagaa agtatccatc   2100

atggctgatg caatgcggcg gctgcatacg cttgatccgg ctacctgccc attcgaccac   2160

caagcgaaac atcgcatcga gcgagcacgt actcggatgg aagccggtct tgtcgatcag   2220

gatgatctgg acgaagagca tcaggggctc gcgccagccg aactgttcgc caggctcaag   2280

gcgcgcatgc ccgacggcga ggatctcgtc gtgatccatg gcgatgcctg cttgccgaat   2340

atcatggtgg aaaatggccg cttttctgga ttcaacgact gtggccggct gggtgtggcg   2400

gaccgctatc aggacatagc gttggatacc cgtgatattg ctgaagagct tggcggcgaa   2460

tgggctgacc gcttcctcgt gctttacggt atcgccgctc ccgattcgca gcgcatcgcc   2520

ttctatcgcc ttcttgacga gttcttctga agctctggta gcaaaacatt tggccggaca   2580

ccactgtaaa cggatgatag tggcgaaccg cacgcgagag cgagctttga gcttagcgca   2640

gcagtttggc gccgacgtca tcgcattaaa tgagatccca gactatttag cgcaagcgga   2700

tattgtgatc agctcgaccg ctagcccttt gcccatcata ggtaaaggca tggtcgaaag   2760

tgcactaaag gcccgtcgcc atcagcctat gttgttggtg gatattgccg tgccacgcga   2820

tattgagccg caggtcggta agcttaacga tgcttatctc tattcggtcg atgacttgca   2880

gtcgattgtc gatagcaata tcgagcagcg caaagtggaa gcgattcagg cagaagcgat   2940

tgtcagtgaa gagagcgcca ccttcatgag ttggatgcgc tcactgcaag cggtggacag   3000

tattcgtgat tatcgtaagc aagccaatga agcgcgtgaa gagctactca ataaaagttt   3060

gcaagcattg gcagcgggtg gcgatcctga aaagctgctc atagaattaa gcaacaaact   3120

gaccaacaaa ctaattcaca ccccaacccg agcgctacaa accgcggcgg aacaaggga    3180

accggctaaa ctggccgtga tcagacaaag tttaggtctt gacgatctga actaaatctc   3240

aacttagagt ttaaagaagc aactatgaaa gcgtcgattt taagcaagct tgaatccctt   3300

gttgagcgct atgaag                                                   3316
```

<210> SEQ ID NO 3
<211> LENGTH: 2200
<212> TYPE: DNA
<213> ORGANISM: Vibrio cholerae

<400> SEQUENCE: 3

```
gacctgtgat gtaaaggaac aggttgagtt tggccggtga aggccacacg gttgtgccgt     60

ggatcatggg agcagcgtcc attgtgagat caccagttga atcgaggttt tattttgctg    120

gagtttaagt ttatcaggca gcggaatggg ctgatgttgc cactcaatcg cttggtaacg    180

ttggtattct acgtgccatt cctccgttga ggcgagtttg gtgagagtgg caagagtgtt    240

ttgttcattc aactcgtaat gggttgcttg ggtcggcaag cctaaaatcc aatcttcaag    300

ctgttcaacg ggaatatcta accctgttaa attgcggatc aggctttgtg catcttggtc    360

gcggtagatt tgatcatcat aagtttcgac ccgcgcacct tgttcatcga cctgtaagtt    420

cagcacggtt tgaccaagaa aattgcttaa acgcagtgag agtttttgtg ggcttttttg    480

ccattgaaag ttgaacgatt gtcgctgatc gggcgcgata tagccgagtt ttccggttaa    540

ttgataatgt tgaatttgtt ctagagtgac ttggtgtgat tgccattgaa cattgacggg    600

ttgtagcggt gcggtggcac aacctgccaa aagcaacaga ctcgccaatc ctggcagtag    660

gcgacgtacg agagcattca tagtgcgttt tttatccaaa gcgagagcga aaacgggcta    720
```

-continued

```
actatatcat tgatctcacg aactcaggaa aacaaatccg gtctgccctt tcaatcaaag    780

agggcatcaa gtaaaattcc gcctctagtc caccacacat atctgagaat cctctataga    840

tgtctttgct tgccattgga atcaatcaca atacggcgtc ggtagaattg cgggaaaaag    900

tggcgttcgg tccagagaag ctctctttgg cgctgaatca gctttccacc agttcacacg    960

ttaaaggagg cgtgatcctc tcaacgtgta accgcaccga aatttattgt gatgtgagat   1020

cagcaagtaa aaacaaagtc atcgaatggt tgtcccagtt tcaccaagtc agcttggatg   1080

agttaaaacc cagcctatac gttcatgaag agcaagccgc cattcgtcat ttgatgcgtg   1140

tcgcctgtgg tttggactct ctagtgttgg gcgagccgca gatattagga caagttaagc   1200

aagcttacgc agaggcgaga gagaatcacg ccgtcaatcc ggcgacggaa aagctgtttc   1260

aaaaggcttt ttcggtcgcg aaacgggtaa gaacagaaac cgaaatcggc ggcagcgcgg   1320

tttcggtcgc ttatgccgct tgcactttag caaaacacat ttttgaatcg ctggccgacg   1380

ctacggtact gttggtcggg gctggtgaaa ccattgaaag tcatttaaat gacttgaact   1440

ggtagcaaaa catttggccg gacaccactg taaacggatg atagtggcga accgcacgcg   1500

agagcgagct ttgagcttag cgcagcagtt tggcgccgac gtcatcgcat taaatgagat   1560

cccagactat ttagcgcaag cggatattgt gatcagctcg accgctagcc ctttgcccat   1620

cataggtaaa ggcatggtcg aaagtgcact aaaggcccgt cgccatcagc ctatgttgtt   1680

ggtggatatt gccgtgccac gcgatattga gccgcaggtc ggtaagctta acgatgctta   1740

tctctattcg gtcgatgact tgcagtcgat tgtcgatagc aatatcgagc agcgcaaagt   1800

ggaagcgatt caggcagaag cgattgtcag tgaagagagc gccaccttca tgagttggat   1860

gcgctcactg caagcggtgg acagtattcg tgattatcgt aagcaagcca atgaagcgcg   1920

tgaagagcta ctcaataaaa gtttgcaagc attggcagcg ggtggcgatc ctgaaaagct   1980

gctcatagaa ttaagcaaca aactgaccaa caaactaatt cacaccccaa cccgagcgct   2040

acaaaccgcg gcggaacaag gggaaccggc taaactggcc gtgatcagac aaagtttagg   2100

tcttgacgat ctgaactaaa tctcaactta gagtttaaag aagcaactat gaaagcgtcg   2160

attttaagca agcttgaatc ccttgttgag cgctatgaag                         2200
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4

```
gacctgtgat gtaaaggaac                                                 20
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5

```
cttcatagcg ctcaacaagg                                                 20
```

<210> SEQ ID NO 6

-continued

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ctgttggtcg gggctggtga a 21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
agcgacgggc ctttagtgc 19

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tcgagctcta gaagcttcag ggcgcaaggg ctgct 35

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tcgagctcta gaagcttcag aagaactcgt caagaag 37

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
agtcatttaa atgattcatt aatgcagctg gc 32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
agtcatttaa atttatttgt agagctcatc ca 32

<210> SEQ ID NO 12
<211> LENGTH: 20

-continued

```
<212> TYPE: DNA
<213> ORGANISM: Unknown Organism
<220> FEATURE:
<223> OTHER INFORMATION: Description of Unknown Organism: Sequence
      derived from unknown source used for mutation purposes

<400> SEQUENCE: 12

tgaaagtcat ttaaatgact                                              20
```

*VIBRIO CHOLERAE* STRAINS VCUSM1 AND VCUSM4, METHOD OF PRODUCING SAME, AND VACCINE DERIVATIVES THEREOF

RELATED APPLICATIONS

This application is a continuation of U.S. patent application Ser. No. 10/981,760 filed Nov. 5, 2004, now abandoned.

FIELD OF INVENTION

The present invention relates to two *Vibrio cholerae* strains, VCUSM1 (O139) and VCUSM4 (El Tor) that have been mutated in the hemA gene. The present invention further relates to methods for developing VCUSM1 (O139) strain and VCUSM4 (El Tor).

BACKGROUND OF THE INVENTION

Introduction

Cholera can be defined as a sudden onset of watery diarrhea often accompanied by vomiting and resulting in hypovolemic shock and acidosis. Cholera is caused by certain members of the species *Vibrio cholerae* which reside in the small intestine and secrete cholera toxins.

*Vibrio cholerae* strains are natural inhabitants of brackish water and estuarine systems where they may constitute the normal microflora of zooplankton and shellfish. *Vibrio cholerae* is the type species of the genus *Vibrio* that belongs to the family Vibrionaceae. *Vibrio cholerae* are facultative anaerobe, highly motile and slightly curved non-sporing, gram negative rods measuring 1.4 to 2.6 μm in length. *Vibrio cholerae* grows optimally in the presence of 5-15 mM sodium ions ($Na^+$) and can tolerate high alkalinity (~pH 10) (Reidl et al., 2002; Faruque et al., 1998; Parsi, 2001; Cooper, 2001; Mooi et al., 1997).

Out of 200 *vibrio* serovars, only *Vibrio cholerae* O1 and O139 have been implicated as causative agent of epidemic and pandemic cholera. It is known that the $5^{th}$ and $6^{th}$ pandemics were caused by *V. cholerae* O1 of classical biotype, but the nature of the strains causing the first four pandemics is not known. Although it is generally believed that the first three pandemics were also caused by classical biotypes. Prior to $7^{th}$ pandemic, the El Tor biotype was thought not to cause cholera, since it was associated with only mild diarrhea. However, it was later confirmed that both, the classical and El Tor biotypes have potential to cause serious cholera.

Non-O1 serotypes were never associated with cholera epidemics, although they have caused local outbreaks. Until mid 1992, it was generally considered that the ongoing seventh pandemic is caused by *Vibrio cholerae* O1. Beginning in October 1992, cases in Madras, India were noted which were associated with a *Vibrio cholerae* strain that did not agglutinate with O1 antisera. Similar cases were subsequently noted in Madurai, Vellore, Calcutta, and in Southern Bangladesh. In the following months, this new strain spread in epidemic form across Bangladesh, with over 100,000 cases reported by the end of March 1993. Cases were also reported from Thailand, Malaysia, Pakistan, and Nepal. For a time being, this new strain replaced *V. cholerae O*1 strain as the predominant cause of cholera in Southeast Asia. It was also isolated from travelers in California, Estonia, Germany, Singapore, and HongKong.

This new strain was later designated as *Vibrio cholerae O*139 synonym Bengal. *V. cholerae O*139 is closely related to the Asian *V. cholerae* O1 El Tor strain; however, it has certain distinctive features. Features that are common between O139 and El Tor are high level of polymyxin B resistance, capability of agglutinating chicken erythrocytes and resistance to infection by Mukhejee's phage. *V. cholerae* O139 does not agglutinate with monoclonal or polyclonal antisera directed against the O1 antigen. These strains appear to lack portion of at least two genes within the O1 biosynthetic gene cluster (Vcrfb) and therefore do not express native O antigen. Analysis of serogroup O1 and O139 isolates has revealed marked differences in their Lipopolysaccharide (LPS). O139 strain appears to have a modified core structure and is usually referred to as a semi-rough LPS and not a smooth LPS like in the O1 strain. Due to the presence of the LPS capsule, the O139 strain is resistant to killing by healthy human serum and has increased potential for invasive disease among persons infected with this organism.

Cholera has re-emerged as a major infectious disease in the recent past, with a global increase in its incidence. People in fifty eight countries across the globe are suffering from cholera pandemic. An estimated of 184,311 cases were reported to WHO with 2,728 death in year 2001 alone; however, officially notified cases do not reflect the overall burden of disease. Most under developing countries deliberately underreport cholera cases due to the fear of travel and trade related sanctions. A careful estimate suggests that some 5-7 million cholera cases occur annually with around 100-120,000 deaths each year.

Despite great efforts made by several countries, cholera is again on the rise. While the disease no longer poses a threat to countries with minimum standards of healthy living conditions, it remains a challenge to countries where access to safe drinking water and adequate sanitation cannot be ensured for all. Almost every developing country is facing either a cholera outbreak or the threat of an epidemic.

Cholera patients who receive adequate treatment mostly always recover rapidly. Treatment of cholera consists essentially of replacing fluid and electrolytes either intravenously or orally. Antimicrobial therapy serves as an important adjunctive therapy.

Due to the practical limitations of the implication of various preventive measures in cholera endemic areas, mass vaccination of the population at risk offers a cheap prophylactic alternative. Attempts of developing cholera vaccine had started from 1884 but with limited success; however, researchers have been able to gather invaluable data from all those earlier attempts.

Cholera Vaccines

The idea that an initial clinical infection gives rise to high level of enduring protection was not appreciated until the pioneering work of Cash et al in 1974 demonstrated that an initial infection with classical *V. cholerae O*1 Inaba, provides solid protection for at least 1 year against re-challenge with the homologous organism. These observations were further expanded by Levine between 1979 and 1983, who demonstrated that an initial clinical infection with the classical biotype *V. cholerae* O1 provides 100% protection against illness following re-challenge with the classical biotype organisms of either serotype for at least 3 years (Levine et al., 1993). However, the same authors reported a 90% protection after the infection with *V. cholerae* O1 El Tor. The authors also noted that no vibrios could be recovered from the excreta of the volunteers who were re-challenged with the classical biotype. In contrast, the authors were able to recover vibrios from co-procultures of approximately one third of the volunteers who were challenged and subsequently re-challenged with El Tor vibrios (Levine et al., 1993 and 1995).

Volunteers orally fed with as little as 0.5 microgram of purified cholera toxin suffer with profuse diarrhea, whereas immunized volunteers while fed with purified cholera toxin don't (Levine et al., 1993 and 1995). This suggests that the presence of anti-cholera toxin antibodies on the surface of the mucosa in the small intestine is capable of neutralizing the cholera toxin thus prevents the onset of the watery diarrhea. On the other hand, immunized volunteers while challenged with homologous virulent *V. cholerae*, shed very little if any virulent vibrios in co-proculture (Levine et al., 1995 and 1993). This clearly suggests that antibodies are present on the surface of the mucosa in the small intestine that neutralize the virulent vibrios thus preventing them from colonizing or secreting cholera toxin in the lumen (Levine et al., 1995 and 1993). Considerable direct and indirect evidence from epidemiological studies, involving human volunteers as well as animal studies points to the existence of both, anti cholera toxin and antibacterial immunity (Bondre et al., 1997; Pierce et al., 1987). These studies have also revealed that a better protection is achieved while using both, the toxin and the somatic antigens that involve a synergistic interplay between antitoxic and antibacterial immune mechanism (Ryan et al., 2000).

Parenteral Cholera Vaccines

Until it was found in mid 1970s that *V. cholerae* is a non-invasive organism, almost all the vaccines developed against cholera were given parenterally. Various type of parenteral vaccines developed include killed whole cell vaccines, toxoid vaccines, and combined whole cell toxoid vaccines.

Killed Whole Cell Parenteral Vaccines

Since 1884, killed whole cell vaccines made with *V. cholerae O*1 have been utilized as parenteral vaccines; however, it was not until early 1960s, that well designed randomized controlled trials to assess the efficacy of these vaccines have been carried out. However, it was found that these vaccines provided with only short term protection and that the protection was also age related (Ryan et al., 2000). Adults afforded better protection than the young children, suggesting that the vaccine worked best in immunologically primed populations by boosting underlying immunity (Ryan et al., 2000). In a few trials, killed whole cell vaccine was administered with adjuvants in hope to enhance the immune response, however, this led to serious local reactions and further trials were abandoned (Ryan et al., 2000; Kalambaheti et al., 1998).

Toxoid Parenteral Vaccines

A number of toxoid vaccines have been developed to be administered parenterally and were intended to protect the vaccinee by eliciting antitoxic immunity.

These include formaldehyde cholera toxoid, gluteraldehyde cholera toxoid, procholeragenoid, and B subunit toxoid vaccine (Ryan et al., 2000; Levine et al., 1995 and 1993).

Formaldehyde Cholera Toxoid Parenteral Vaccine

It was found that the treatment of purified cholera toxin with formaldehyde could eliminate its toxicity without compromising its ability to stimulate anti-toxin antibodies (Ryan et al., 2000). A prototype vaccine candidate was prepared with alum adjuvant and administered to volunteers in Bangladesh. The vaccine prototype elicited significant levels of antitoxin IgG without severe local reaction at the site of injection. However, field trials to assess the efficacy of this vaccine were never initiated (Ryan et al., 2000; Levine et al., 1995 and 1993). A modification of this vaccine prototype was prepared using formalin and glycine and termed lot 11. A large scale field trial was conducted in Philippines but no beneficial effects were detected, therefore, further trials were abandoned (Ryan et al., 2000; Levine et al., 1995 and 1993).

Gluteraldehyde Cholera Toxoid Parenteral Vaccine

A gluteraldehyde treated cholera toxoid vaccine was prepared in the hope of getting a somatic antigen free toxoid vaccine. Field trials conducted in Bangladesh in parallel to a killed whole cell vaccine and a subunit vaccine revealed little protection afforded by this vaccine candidate. Accordingly, no further trials were conducted (Ryan et al., 2000; Levine et al., 1995 and 1993).

Procholeragenoid Parenteral Vaccine

Purified cholera toxin heated at 65° C. for 5 minutes followed by formaldehyde treatment yields procholeragenoid, a high molecular weight toxoid that retains its immunogenic potential without any toxicity. Studies conducted in rabbit model have revealed high serum antitoxic IgG titers comparable to titers obtained with untreated cholera toxin. However, this vaccine prototype has never been tried in humans (Levine et al., 1993; Germanier et al., 1976 & 1977).

B Subunit Toxoid Parenteral Vaccine

Biological activity of whole cholera toxin is due to it's A subunit, whereas B subunit is potentially immunogenic. Since B subunit is highly immunogenic and has no toxic activity, it represents an attractive immunogen to stimulate antitoxic immunity. While administered in human volunteers, the B subunit toxoid vaccine exhibited high titers of antitoxic antibodies in the serum; however, the immunity was higher in immunologically primed populations (Ryan et al., 2000; Levine et al., 1993; Sack et al., 1991).

Bacterial Subunit Parenteral Vaccines

Bacterial subunits such as LPS have also been administered parenterally to elicit the immune response. One such vaccine prototype was prepared using purified Ogawa and Inaba LPS-protein extract. The efficacy of this prototype was evaluated in Bangladesh where Ogawa LPS vaccine yielded almost similar efficacy as killed whole cell vaccine. Similarly in another field trial, Inaba LPS vaccine provided a level of protection as high as that conferred by the Inaba whole cell vaccine (Ryan et al., 2000; Levine et al., 1993; Sack et al., 1991).

Combined Whole Cell Toxoid Parenteral Vaccines

In the 1970s, Welcome Research Laboratories prepared a combined whole cell toxoid vaccine administered parenterally with alum adjuvant. The combination vaccine stimulated excellent serum vibriocidal and antitoxic responses; however, this vaccine prototype was never evaluated for its efficacy in large scale controlled field trials (Ryan et al., 2000; Levine et al., 1993; Sack et al., 1991).

Oral Cholera Vaccines

Until 1970, the majority of cholera vaccines were developed for parenteral administration, nevertheless, few cholera vaccines were also developed for oral administration. However, earlier trials with oral cholera vaccines were empirical and not based on immunological principles. From the mid 1970s, researchers started appreciating the role of oral immunization based on the fact that natural infection with *V. cholerae* elicits high level of protection that lasts for at least 3 years.

Killed Whole Cell Oral Vaccines

Modern history of orally administrable killed whole cell vaccines starts in 1962 when Freter et al., 1962 reported 77% efficacy of this whole cell vaccine in North American volunteers. Cash in 1974, evaluated the efficacy of a whole cell vaccine composed of $1.6\times10^{10}$ killed Ogawa and Inaba O1 vibrios in North American volunteers with an efficacy of 61%. A Swedish killed whole cell vaccine composed of $2\times10^{11}$ heat and formalin killed Ogawa and Inaba O1 vibrios have also been extensively evaluated in North American and Swedish adults and in Bangladeshi adults and children. The vaccine did not cause any side effects and a significant rise in serum vibriocidal antibodies was seen in 80% of volunteers. Clemens has reported a 52% vaccine efficacy of a whole cell killed vaccine for at least 36 months in a controlled field trial in Bangladesh (Clemens et al., 1988 & 1990).

Bacterial Fraction Oral Vaccine

A bacterial fraction vaccine has been prepared by treating the outer membrane of *V. cholerae* with trichloroacetic acid. The antigenic complex thus extracted was referred to as CH1+2. This vaccine candidate was evaluated in a field trial in Zaire with a total of 18,623 individuals vaccinated. The vaccine was found to elicit good immune response. This vaccine has not been evaluated for efficacy in other field trials (Fournier 1998).

Gluteraldehyde Cholera Toxoid Oral Vaccine

North American volunteers were orally vaccinated with three doses of 2 mg of gluteraldehyde treated toxoid 1 month apart or three 8.0 mg oral doses with $NaHCO_3$ at 1 month intervals. No adverse effects were observed, however, when experimental challenge studies were carried out to assess the protective efficacy, no significant protection was observed (Ryan et al., 2000; Levine et al., 1993).

B Subunit Toxoid Oral Vaccine

Swedish and Bangladeshi volunteers were vaccinated orally with the B subunit of highly purified cholera toxin with or without sodium bicarbonate ($NaHCO_3$).The vaccine candidate caused no reactogenic side effects and stimulated high titers of antitoxin antibodies in serum, saliva and breast milk. Administration with $NaHCO_3$ or other gastric acidity neutralizing buffer enhanced the immune response. Large-scale field trials with the B subunit alone were not conducted; however, it has been evaluated extensively in combination with whole cell killed oral vaccine (Ryan et al., 2000; Levine et al., 1993).

Combination Oral Vaccines

Three different killed whole cell vaccines have been tried in combination with toxoid as oral vaccines. These include (i) gluteraldehyde cholera toxoid combined with alcohol killed O1 vibrios, (ii) procholeragenoid combined with heat and formalin killed O1 vibrios and (iii) B subunit combined with heat or formaldehyde inactivated O1 vibrios. All three combinations were well tolerated by the volunteers. However, the B subunit combined with killed whole cells gave the best immune response. Significant rises in serum vibriocidal antibodies were seen in 89% of the vaccinees. In another study, the B subunit/killed whole cell combination vaccine was compared with oral whole cell vaccine alone. A total of 63,498 individuals were recruited for a randomized, double blind placebo controlled trial in Bangladesh. During the first six months of surveillance the level of protection provided by the combination vaccine was significantly higher than that of whole cell vaccine alone (85% vs 65%). After 12 months of surveillance, the level of protection was 62% vs 53% for combination vaccine and whole cell killed vaccine respectively. During the first six months, the combination vaccine protection was similar in young children as well as in older children and adults. However after six months, the level of protection dropped appreciably in children less than six years old (Ryan et al., 2000; Taylor et al., 1999; Concha et al, 1995; Jertborn et al., 1996).

Despite the significant advantages of this combination vaccine, it nonetheless had drawbacks that limited its use. First it has transient protection in the young children, the group which is most susceptible to cholera infection. Second the cost involved in the preparation of the vaccine. Third is the requirement for multiple (at least two) spaced doses to prime and boost the immune response.

Live Oral Vaccines

For many years, some investigators have favored the concept of live oral vaccine as it best mimics the natural infection. It is also well established that only the natural infection provides with best protection for at least three years. Many live oral vaccines have been developed and evaluated in human volunteers for their efficacy.

Environmental Strains as Live Oral Vaccines

A number of non-enterotoxigenic *V. cholerae* O1 strains have been isolated from the environment and have been evaluated in volunteers for their efficacy to elicit immunity. The results were generally disappointing as most of these environmental strains were poor colonizers of the small intestine and therefore were unable to evoke immune response.

Chemically Mutated Attenuated Strains as Live Oral Vaccines

Before the advent of modern tools to engineer the DNA, mutations were generally made by exposing the DNA to mutagenizing chemicals such as nitrosoguanidine. Two such strains of *V. cholerae* attenuated by mutagenizing agent nitrosoguanidine are M13 and Texas Star-SR. M13 was prepared from pathogenic classical Inaba 569B. When given orally to the volunteers, M13 did not cause any diarrhea, and elicited moderate but significant level of protection against challenge with pathogenic *V. cholerae* O1.

Texas Star-SR was an $A^-B^+$ mutant derived from El Tor Ogawa strain 3083. Texas Star-SR was mildly reactogenic in volunteers; however, it provided moderate but significant protection against challenge with either serotype of El Tor. Texas Star-SR suffered from certain inherent drawbacks, i.e. mutagenesis with nitrosoguanidine is known to induce multiple mutations, and the precise genetic lesion presumed responsible for the attenuation was unknown. Therefore, there always remained the theoretical possibility that it could revert to virulence.

Attenuated Mutants Prepared by Recombinant DNA Technique

It has generally been accepted that diarrhea is caused by the cholera toxin. And therefore, mutating or deleting the whole gene coding for cholera toxin or mutating the gene coding for the biologically active A subunit would be sufficient to make a vaccine strain non-toxic. Based on this hypothesis, a number of vaccine strains have been constructed such as JBK70, CVD101, CVD103, CVD104, CVD105, O395-N1.

JBK70 was a $A^-B^-$ strain originally derived from the toxigenic N16961 strain. In human volunteers it did not cause severe diarrhea and elicited high titers of vibriocidal antibodies. When the vaccines were challenged with the virulent N16961, only 1 out of 10 vaccinees developed severe diarrhea as compared to 7 out of 8 non-vaccinated individuals. Thus 89% of protection was achieved. Further studies with JBK70 were halted due to mild diarrhea experienced by most of the volunteers (Ryan et al., 2000; Levine et al., 1993).

Since JBK70 was mildly reactogenic, in order to ascertain whether this reactogenicity was associated with the El Tor strain, a vaccine strain CVD101 was developed (Ryan et al., 2000; Levine et al., 1993). CVD101 was a $A^-B^+$ strain derived from classical Ogawa 395 strain (Ryan et al., 2000;

Levine et al., 1993). When orally administered to the volunteers, 40-60% of volunteers still developed mild diarrhea. However, both the antitoxin and vibriocidal titers were comparable to that achieved with the toxigenic parent strains (Ryan et al., 2000; Levine et al., 1993). Although able to evoke very good immune response, both the JBK70 and CVD101 caused mild diarrhea in the volunteers. This indicated that *V. cholerae* of either serotype secrete some toxin other than cholera toxin that is responsible for the residual reactogenicity. Suggested candidates for this effect were the hemolysin/cytotoxin, cytotoxin/protease, or shiga like toxin (Ryan et al., 2000; Levine et al., 1993).

In order to investigate this hypothesis, gene coding for hemolysin was deleted from JBK70 and CVD101 resulting in strains CVD104 and CVD105 respectively. While orally fed, volunteers still suffered with mild diarrhea. All vaccinees shed the vaccine strain and the immune response was satisfactory (Ryan et al., 2000; Levine et al., 1993; Kaper et al., 1990).

In an effort to develop a non-toxigenic vaccine strain, an $A^-B^+$ strain was derived from the classical Inaba 569B that does not elaborate Shiga like toxin and was designated as CVD103 (Kaper et al., 1990). CVD103 did not cause diarrhea when given to the volunteers and it elicited good vibriocidal as well as antitoxic immunity after a single dose. At high doses of $1\times10^8$ cells, only 5 out of 46 volunteers developed mild diarrhea and out of 5, only one volunteer had stool volume that exceeded 400 ml. In contrast to JBK70, CVD101 and O395-N1, that frequently resulted in malaise, anorexia, and abdominal cramps, these symptoms were never recorded among volunteers who received CVD103 (Kaper et al., 1990). In order to distinguish the mutant from the wild type, a mercury resistant gene was cloned onto the hlyA locus of CVD103, thus obtained CVD103-HgR. An initial study with CVD103-HgR was conducted in 18 North American volunteers. No one experienced adverse reactions and less organisms were recovered from the co-procultures as compared to CVD103. Nevertheless, CVD103-HgR colonized the small intestine and elicited the vibriocidal antibodies and antitoxic antibodies similar to those who were vaccinated with parent CVD103 (Cryz et al., 1995). Based on the encouraging studies done with North American volunteers, studies were initiated with volunteers in several countries in Africa, Asia and Latin America. Experimental challenge studies in volunteers demonstrated protection as early as 1 week after vaccination. A high level of protection (>90%) was conferred against moderate and severe cholera caused by challenge with *V. cholerae O*1 of either El Tor or classical biotype. The overall protective effect against El Tor cholera of any severity was 80% (Ryan et al., 2000).

A few limitations associated with CVD103-HgR include the lack of evidence whether this vaccine confers any protection in children aged below 2 years. Furthermore CVD103-HgR would not be expected to confer protection against *V. cholerae O*139 (Ryan et al., 2000).

The following US patent disclose different strains of *Vibrio cholerae* and vaccine derived therefrom: U.S. Pat. Nos. 4,264,737; 4,666,837; 4,882,278; 5,631,010; 5,882,653; 4,935,364; 5,098,998.

SUMMARY OF THE INVENTION

The present invention relates to *Vibrio cholerae* strains, VCUSM1(O139) and VCUSM4 (El Tor). This vaccine strains has been mutated in the hemA gene (for VCUSM1). The hemA gene VCUSM4 is mutated by frame shift mutation. Both the strains are not capable of synthesizing aminolevulinic acid (ALA) de novo. The strains are obtained from a parent strain originally isolated from a patient's coproculture having all the identifying characteristics of *Vibrio cholerae O*139 synonym Bengal as comma-shape, highly motile, Gram negative, optimal growth at Ph of 6-9, agglutinable with anti O139 antisera, non-agglutinable with anti O1 antisera, has intact genes of ctx, ace and zot and produces functional cholera toxin, accessory cholera enterotoxin and zonula occludes toxin. The mutation was carried out by inserting a kanamycin resistance gene ($kan^R$) cassette in the hemA gene. These hemA mutants grow only in the presence of amino levulenic acid (ALA) and have limited in vitro and in vivo growth in the absence of ALA. VCUSM1 and VCUSM4 strains have been tested for their colonization ability in the infant mouse model. Their colonization ability was good and was similar as that of wild type *V. cholerae*. The protective efficacy of the VCUSM1 and VCUSM4 strains were tested in the RITARD (removable intestinal tie-adult rabbit diarrhea) model. All of the vaccinated rabbits survived with no symptoms of diarrhea after challenge with virulent *Vibrio cholerae*, whereas 100% mortality was observed in unvaccinated (control) rabbits within 18 hours post challenge. The vaccine strains also did not survive in environmental waters like the sea, river and sewage when compared to wild type *V. cholerae*. These results indicate that the VCUSM1 and VCUSM4 do not survive in the environment; hence they have good safety properties. The strains developed in the present invention offers a way to develop vaccines for cholera caused by *V. cholerae O*139 and O1 serotype and El Tor biotype.

The invention will be described in detail with reference to the preferred embodiments and to the following figures by way of example and not limiting in any manner.

BRIEF DESCRIPTION OF THE FIGURES

Figure 1:
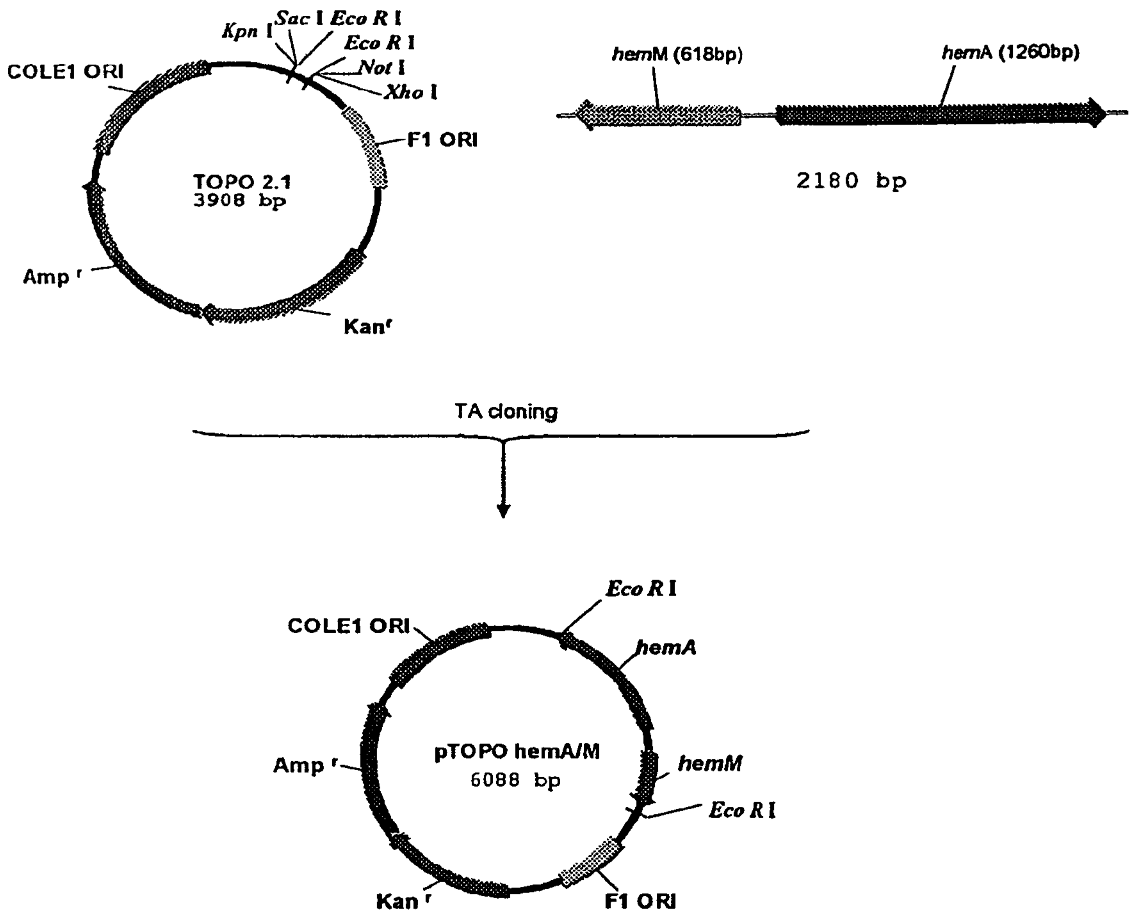

Detailed description of the figures is given in the text.

FIG. 1

PCR amplification of 2180 by hemA/M from *V. cholerae* and subsequent cloning onto a PCR cloning vector, pTOPO (INVITROGEN®, California).

FIG. 2

Subcloning of hemA/M gene from pTOPO onto a shuttle vector pARO180 and subsequent insertion of $kan^R$ into the hemA gene by blunt end ligation.

FIG. 3

Subcloning of the hemA/M mutated with $kan^R$ onto a suicidal vector pWM91.

FIG. 4

Subcloning of the hemA/M gene from pTOPO onto a shuttle vector pARO180 and subsequent insertion of GFP into the hemA gene by blunt end ligation.

FIG. 5

Subcloning of the hemA/M mutated with GFP onto a suicidal vector pWM91, subsequent deletion of GFP from pWM91-hemA/M-GFP and formation of pWM91-hemA*/M with frameshift mutation in hemA.

DESCRIPTION OF SPECIFIC EMBODIMENTS

VCUSM1 (O139 Bengal)

The inventors had constructed a metabolic auxotroph of *V. cholerae* O139 by mutating its hemA gene through insertion of a $kan^R$ gene cassette. The mutant was obtained after replacing the chromosomal hemA gene in *V. cholerae O*139 with the hemA::kan allele present on pWM91 suicide vector as described in Example 1. Mutants were rigorously checked for the curing of suicide plasmid by growing the clones on LB agar plates with various combinations of antibiotics. The hemA::kan mutant thus obtained was sensitive to ampicillin, resistant to kanamycin and required ALA for normal growth and was designated as VCUSM1. The presence of hemA::kan was confirmed by PCR and sequencing.

To determine whether successive genetic manipulations had any unexpected effects over the important characteristics of cholera vaccine candidate, the inventors compared mutants with wild type for their growth rate as well as for motility.

Cells that were not coasted were able to multiply up to 12 hours in the absence of exogenous ALA whereas cells that were coasted for 6 and 12 hours did not multiply at all. The data suggests that if the cells are not coasted, they have enough cellular ALA that can support their growth up to 12 hours after which the ALA is exhausted and cells stop multiplying. Minimal coasting time was found to be 6 hours. Optimal concentration of ALA that gave comparable growth to wild type was found to be 40 μg/ml. Higher concentration of ALA had no positive or negative effect on the growth of VCUSM1. Both the wild type and VCUSM1 reached to the stationary phase of their growth at 10 hours after which there was no increase in the absorbance ($A600_{mn}$). VCUSM1 and wild type grown under static conditions reached to the stationary phase of their growth at 6 hour and no increase in absorbance ($A600_{nm}$) was observed thereafter. Under microaerophilic conditions, in the absence of ALA, the difference in growth between wild type and VCUSM1 was less pronounced.

To determine whether mutation of hemA had any effect on motility of the bacteria, motility of VCUSM1 was checked on motility plates and compared with wild type strain. When supplemented with 40 μg/ml of ALA, VCUSM1 spread through soft agar to an average diameter of 13 mm as compared to 16 mm of wild type in 24 hours, whereas in the absence of ALA, VCUSM1 spread to an average diameter of 5 mm only. These findings suggest that VCUSM1 was 20% less motile as compared to wild type. However, motility is considered an important virulence factor and hyper motile vibrios are generally more toxic owing to their ability to colonize small intestine better than average or hypo motile vibrios. A reduction of motility in VCUSM1 should lead to the reduction of colonization potential hence reduced toxicity.

Since colonization is critical for development of a protective immune response, the inventors compared the colonization potential of VCUSM1 with wild type. Infant mice were inoculated with $1\times10^6$ cfu of either VCUSM1 or wild type. After 18 hours, an average of $2\times10^7$ cfu was recovered from each gut of mice inoculated with VCUSM1 and $1\times10^8$ cfu of wild type. Although recovery of VCUSM1 was five fold less as compared to wild type, it did colonize and multiply in the small intestine of infant mice. Recovery of VCUSM-1 from the small intestine of mice is comparable (5 fold vs 5.6 fold) to a thymidine auxotroph of *V. cholerae* El Tor (Valle et al., 2000) and superior (5 fold vs 44 fold) to a recently reported O139 thymidine auxotroph L912T (ΔCTXΦ hapA::celA and thyA mutation) (Ledon et al., 2003). Reduction of colonization is also indicative of reduction in toxicity that was later confirmed by the rabbit ligated ileal loop model.

While VCUSM1 was limited in its growth in vivo, rabbits vaccinated with VCUSM1 had only a slightly lower anti-CT IgG and IgA titers (mean titer IgG=575, IgA=175) as compared to the animals vaccinated with wild type (mean titer IgG=610, IgA=160), although the difference is not statistically different from 0 day to 14 day. This clearly showed the immunogenic potential of the present vaccine strain.

Comparable vibriocidal antibody titers were obtained in the animals vaccinated with VCUSM1 or wild type. Again, these findings are comparable (325 vs 368) to a thymidine auxotroph of *V. cholerae* El Tor (Valle et al., 2000) and superior (325 vs 127) to O139 auxotrophic mutants L912T (Ledon et al., 2003).

Vaccinated and unvaccinated rabbits were challenged with intraduodenal injection of $10^{11}$ virulent O139 Bengal. Rabbits vaccinated with VCUSM1 or wild type survived the challenge and showed no signs of diarrhea during 5 days of observation period whereas unvaccinated rabbits died within 18 hours post challenge. Dead animals were autopsied and their small intestines were found to have large volumes (up to 50 ml of rice watery fluid. This rice watery fluid was culture positive for O139 Bengal on TCBS plates (Table 1).

TABLE 1

Outcome of Challenge with Wild Type Using RITARD (removable intestinal tie-adult rabbit diarrhea)

| Sample | Normal Stool | Soft Stool | Mild Diarrhea | Severe Diarrhea | Death |
|---|---|---|---|---|---|
| Rabbit Vaccinated with VCUSM1 n = 4 | 1 of 4 | 3 of 4 | 0 of 4 | 0 of 4 | 0 of 4 |
| Rabbit Vaccinated with Wild Type O139 n = 2 | 2 of 2 | 0 of 2 | 0 of 2 | 0 of 2 | 0 of 2 |
| Control Unvaccinated Rabbit n = 2 | 0 of 2 | 0 of 2 | 0 of 2 | 2 of 2 | 2 of 2 |

Vaccine dose = $1 \times 10^{10}$ bacteria on day 0 & 14

Challenge dose = $1 \times 10^{11}$ wild type O139 on day 35

In ligated ileal loop assay, no fluid was seen in the loops injected with $10^4$-$10^5$ VCUSM1 whereas loops injected with $10^6$ and $10^7$ had 30-50% less fluid as compared to the loops injected with the similar number of wild type. Another important observation was the presence of blood in the loops injected with $10^6$-$10^7$ O139 Bengal showing that the wild type had caused necrosis in the intestinal loops. No such effect was seen in the loops injected with VCUSM1 at the similar dose, which is consistent with reduced toxicity.

Since VCUSM1 was found to be absolutely non-reactogenic at doses of $10^2$-$10^4$ in ileal loop model, the inventors did a dose optimization study. Rabbits were vaccinated with $10^5$-$10^8$ VCUSM1 and serum anti-CT IgG and IgA were determined. An increase in antibody titer was observed with the increase in vaccine dose. Vaccinated rabbits were subjected to challenge studies and inoculated with lethal dose of $5\times10^9$ of the wild type strain. Rabbits vaccinated with $1\times10^6$-$1\times10^8$ VCUSM1 survived the infection and showed no signs of severe diarrhea whereas a 50% protection was achieved in rabbits vaccinated with $1\times10^5$ VCUSM1 (Table 2). This showed that a dose capable of eliciting reasonable immunological response and subsequent protection at acceptable level of reactogenicity is possible to find.

TABLE 2

Dose Optimization Studies; Outcome of Challenge with Wild Type Using RITARD (removable intestinal tie-adult rabbit diarrhea)

| Sample | Normal Stool | Soft Stool | Mild Diarrhea | Severe Diarrhea | Death |
|---|---|---|---|---|---|
| Rabbit Vaccinated with $1 \times 10^5$ VCUSM1 N = 2 | 0 of 2 | 0 of 2 | 1 of 2 | 0 of 2 | 1 of 2 |
| Rabbit Vaccinated with $1 \times 10^6$ VCUSM1 N = 2 | 0 of 2 | 0 of 2 | 2 of 2 | 0 of 2 | 0 of 2 |
| Rabbit Vaccinated with $1 \times 10^7$ VCUSM1 N = 2 | 0 of 2 | 2 of 2 | 0 of 2 | 0 of 2 | 0 of 2 |
| Rabbit Vaccinated with $1 \times 10^8$ VCUSM1 N = 2 | 1 of 2 | 1 of 2 | 0 of 2 | 0 of 2 | 0 of 2 |
| Control Unvaccinated Rabbit N = 2 | 0 of 2 | 0 of 2 | 0 of 2 | 2 of 2 | 2 of 2 |

Challenge dose = $5 \times 10^9$ Wild Type O139 on day 35

Since an ideal cholera vaccine strain should not be able to survive in the environment, one important goal in developing the VCUSM1 was enhancement of the environmental safety parameters. The inventors have evaluated VCUSM1 for its survival in various water samples i.e. sea, river, well, tap and sewage water. Both, VCUSM1 and wild type were limited in growth in well, tap and sewage water but the wild type survived twice as long as VCUSM1 in these water samples. These results were expected for well and tap water since they are not rich in nutrients. However, the inventors also found that sewage water was also not supportive for the growth of vibrios. Perhaps sewage water contained some toxic matter inhibiting the growth of vibrios. A better growth was observed in river and sea water. Again, VCUSM1 was severely limited in growth and no VCUSM1 could be detected beyond 8 days in these relatively nutrient rich water samples. Wild type was detectable even on the 20$^{th}$ day post inoculation. Biological containment of VCUSM1 is better (8 days vs 18 days) as compared to thymidine auxotroph of *V. cholerae* El Tor (Valle et al., 2000). These results clearly indicated that VCUSM1 is an environmentally safer vaccine strain and its chance to survive in the environment is very low.

The live attenuated vaccine strain VCUSM1 described herein has many of the important characteristics required for effective and safe oral cholera vaccine. Although the present vaccine strain still retains the toxin genes and is reactogenic at higher doses, it is able to evoke good immune response and subsequent protection at safer lower doses. Most vaccine strains are constructed with deletion of one or more toxin genes in order to make them less or non-reactogenic. However, several studies have suggested that a combination of somatic antigen and cholera toxin induces a much higher degree of protection in experimental animals than either of the two antigens alone (Ryan et al., 2000; Levine et al., 1995; Levine et al., 1993). This is also supported by the fact that the best protection is achieved by natural infection and patients recovered from cholera are solidly immune for at least three years (Clemens et al., 1987). Serological responses after an episode of cholera occur to the bacterial LPS/CPS and CT. The anti LPS/CPS antibodies likely block colonization, whereas antitoxin antibodies neutralize the cholera toxin. Most of the vaccines with deletions of entire cluster of toxin/s producing genes or producing inactive CT do elicit high titers of vibriocidal antibodies (Ryan et al., 2000). The best known immunological correlate of protection, however, this protection lasts for 6-12 months in contrast to two to three years which is achieved after a natural infection (Clemens et al., 1988). Using naturally occurring immune protection as the gold standard, an ideal cholera vaccine should stimulate at least comparable immune response. Since such vaccine strains would be toxigenic and would develop mild to severe diarrhea. A compromise that might combine some of the advantages of a live vaccine, while avoiding the problem of residual cholera could be the use of auxotrophic mutants as a live oral vaccine. These metabolic auxotrophs would be dependant on substrates unavailable in the human intestine, therefore their proliferation could be controlled and they would be well tolerated. Moreover, since they would be living bacteria, they would interact effectively with the gut immune system. The inventors achieved this goal by a careful selection of vaccination dose capable of evoking reasonable immune response with very little reactogenicity.

VCUSM1 is a life vaccine strain and is administrable orally to subjects. The strain is capable of eliciting high titers of IgG and IgA against cholerae toxin immune response against various surface antigens of *V. cholerae* 0139. The strain is capable of eliciting high titers of IgG and IgA against lipopolysaccharide (LPS) and capsular polysaccharide (CPS) and is capable eliciting high titers vibriocidal antibodies and capable of eliciting high immunological response due to the synergistic interplay of toxin and somatic antigens. VCUSM1 is used to protect vaccines from infection *V. cholerae* 0139 synonym Bengal. VCUSM1 is lyophilized and reconstituted with appropriate buffer for oral consumption. VCUSM1 derivative is used as vaccine to provide protection against *V. cholerae* 0139.

VCUSM4 (O1 El Tor Ogawa)

The inventors have also constructed a metabolic auxotroph of *V. cholerae* O1 El Tor by mutating its hemA gene by frame shift mutation. The mutant was obtained after replacing the chromosomal hemA gene in *V. cholerae* El Tor with the hemA with a frame shift mutation allele present on pWM91 suicide vector as described in Example 2. Mutant was rigorously checked for the curing of suicide plasmid by growing the clones on LB agar plates supplemented with various combinations of antibiotics. The hemA mutant thus obtained was sensitive to ampicillin, sensitive to kanamycin and required ALA for normal growth and designated as VCUSM4. The presence of hemA was confirmed by PCR and sequencing.

To determine whether successive genetic manipulations had any untoward effects on the important characteristics of cholera vaccine candidate, the inventors compared mutants with wild type for their growth rate as well as for motili Cells that were not coasted were able to multiply up to 8 hours in the absence of exogenous ALA whereas cells that were coasted for 6 and 12 hours did not multiply at all. The data suggests that if the cells are not coasted, they have enough cellular ALA that can support their growth up to 8 hours after which the ALA is exhausted and cells stop multiplying. Minimal coasting time was found to be 6 hours. Optimal concentration of ALA that gave comparable growth to wild type was found to be 80 μg/ml. Higher concentration of ALA had no positive or negative effect on the growth of VCUSM4. Both the wild type and VCUSM4 reached to the stationary phase of their growth at 10 hour after which there was no increase in the absorbance ($A600_{nm}$). VCUSM4 and wild type grown under static conditions reached to the stationary phase of their growth at 6 hour and no increase in absorbance ($A600_{nm}$) was observed thereafter. Under microaerophilic conditions, in the absence of ALA, the difference in growth between wild type and VCUSM4 was less pronounced.

To determine whether mutation of hemA had any effect on motility of the bacteria, motility of VCUSM4 was checked on motility plates and compared with wild type. While supplemented with 80 μg/ml of ALA, VCUSM4 spread through soft agar to an average diameter of 12 mm as compared to 15 mm of wild type in 24 hours at room temperature, whereas in the absence of ALA, VCUSM4 spread to an average diameter of 3.5 mm only. These finding suggest that VCUSM4 was 23% less motile as compared to wild type. However, motility is considered an important virulence factor and hyper motile vibrios are generally more toxic owing to their ability to colonize small intestine better than average or hypo motile vibrios. A reduction of motility in VCUSM4 should lead to the reduction of colonization potential hence reduced toxicity.

It is well established that intestinal colonization is critical for the development of protective immune response, the inventors compared the colonization potential of VCUSM4 with the wild type. Infant mice were inoculated with $1\times10^6$ cfu of either VCUSM4 or wild type. After 18 hours, an average of $1.75\times10^7$ cfu was recovered from each gut of mice inoculated with VCUSM4 and $1.2\times10^8$ cfu of wild type. Although recovery of VCUSM4 was five fold less as compared to wild type, it did colonize and multiply in the small intestine of 5 days old infant mice. Recovery of VCUSM4 from small intestine of mice is comparable (5 fold vs 5.6 fold) to a thymidine auxotroph of *V. cholerae* El Tor (Valle et al., 2000) and superior (5 fold vs 44 fold) to a recently reported O139 thymidine auxotroph L912T (ΔCTXΦ hapA::celA and thyA mutation) (Ledon et al., 2003). Reduction of colonization is also indicative of reduction in toxicity that was later confirmed by rabbit ligated ileal loop model.

Although VCUSM4 was limited in its growth in vivo, rabbits vaccinated with VCUSM4 had slightly lower anti-CT IgG and IgA titers (mean titer IgG=525, IgA=125) as compared to the animals vaccinated with wild type (mean titer IgG=655, IgA=153), although the difference is not statistically different from 0 day to 14 day. This clearly showed the immunogenic potential of VCUSM4.

Comparable vibriocidal antibody titers were obtained in the animals vaccinated with VCUSM4 or wild type. Again these findings are comparable (305 vs 368) to a thymidine auxotroph of *V. cholerae* El Tor (Valle et al., 2000) and superior (275 vs 127) to O139 auxotrophic mutants L912T (Ledon et al., 2003).

Vaccinated and unvaccinated rabbits were challenged with intraduodenal injection of $10^{10}$ virulent O1 El Tor. Rabbits vaccinated with VCUSM4 or wild type survived the challenge and showed no signs of diarrhea during 5 days observation period whereas unvaccinated rabbits died within 18 hours post challenge. Dead animals were autopsied and their small intestines were found to have large volumes (up to 60 ml of rice fluid. This rice fluid was culture positive for O1 El Tor on TCBS plates (Table 3).

TABLE 3

Outcome of Challenge with Wild Type Using RITARD (removable intestinal tie-adult rabbit diarrhea)

| Sample | Normal Stool | Soft Stool | Mild Diarrhea | Severe Diarrhea | Death |
|---|---|---|---|---|---|
| Rabbit Vaccinated with VCUSM4 n = 4 | 2 of 4 | 2 of 4 | 0 of 4 | 0 of 4 | 0 of 4 |
| Rabbit Vaccinated with Wild Type O1 El Tor n = 2 | 2 of 2 | 0 of 2 | 0 of 2 | 0 of 2 | 0 of 2 |
| Control Unvaccinated Rabbit n = 2 | 0 of 2 | 0 of 2 | 0 of 2 | 2 of 2 | 2 of 2 |

Vaccine dose = $1\times10^{10}$ bacteria on day 0 & 14
Challenge dose = $1\times10^{10}$ wild type O1 El Tor on day 35

No fluid was seen in the loops injected with $10^2$-$10^5$ VCUSM4 whereas loops injected with $10^6$ and $10^7$ had 25-50% less fluid as compared to the loops injected with the similar number of wild type.

Since an ideal cholera vaccine strain should not be able to survive in the environment, one important goal in developing the VCUSM4 was enhancement of the environmental safety parameters. The inventors have evaluated VCUSM4 for its survival in various water samples i.e. sea, river, well, tap and sewage water. Both, VCUSM4 and wild type were limited in growth in well, tap and sewage water. Although wild type survived twice as long as VCUSM4 in these water samples. It is obvious for well and tap water since they contain less nutrients. However, the inventors were expecting some growth in the sewage water but it was also not supportive for the growth. The inventors think that sewage water contained some toxic matter that inhibited the growth of the vibrios. A better growth was observed in river and sea water. Again, VCUSM4 was severely limited in growth and no VCUSM4 could be detected beyond 7 days in these relatively nutrient rich water samples. Wild type was detectable even on $20^{th}$ day post inoculation. Biological containment of VCUSM4 is better (7 days vs 18 days) as compared to thymidine auxotroph of *V. cholerae* El Tor (Valle et al., 2000). These results clearly indicated that VCUSM4 is environmentally safer vaccine strain and its chances of survival in the environment are scarce.

VCUSM4 is a life vaccine strain and is administrable orally to subjects. The strain is capable of eliciting high titers of IgG and IgA against cholera toxin and is capable of eliciting immune response against various surface antigens of *V. cholerae* O1 El Tor and is capable of eliciting high titers of IgG and IgA against lipopolysaccharide (LPS) of *V. cholerae* O1 El Tor and is capable of eliciting high titers of vibriocidal antibodies and is capable of eliciting high immunological response due to the synergistic interplay of toxin and somatic antigens and is capable of protecting the vaccines from infection with *V. cholerae* O1 El Tor. The VCUSM4 is lyophilized and reconstituted with appropriate buffer for oral consumption. VCUSM4 deravative is used as a vaccine to provide protection against *V. cholerae* 01 El Tor.

The metabolic auxotroph as described herein in respect of VCUSM1 and VCUSM4 can be formulated as a bivalent vaccine to provide protection against *V. cholerae* 0139 synonym Bengal and 01 El Tor.

EXAMPLES

Methodology

Construction of VCUSM1 Strain

For the first time in the literature, the hemA gene, which encodes glutamyl t-RNA reductase has been isolated and cloned by the inventors (Seq. ID No. 1). The hemA gene plays a major rate-limiting step in δ-Aminolevulinic acid (ALA) synthesis. Since ALA is essential for tetrapyrrole biosynthesis, mutation of hemA gene in *V. cholerae* leads to depletion of ALA, which in turn leads to limited growth in normal in-vitro and in vivo condition.

The hemA/M gene was amplified using polymerase chain reaction (PCR) using a forward primer VHF 5' GACCTGTGATGTAAAGGAAC 3' (Seq. ID No.4) and a reverse primer VHR 5' CTTCATAGCGCTCAACAAGG 3' (Seq. ID No.5). The PCR conditions were 95° C. for 3 minutes, 95° C. for 30 seconds, 58° C. for 30 seconds, 72° C. for 45 seconds. 72° C. for 5 minutes. Total numbers of cycles were 30. Wild type O139 bacterial lysate was used as template for PCR.

A 2180 bp PCR product (Seq. ID No.1) was expected. The PCR product was confirmed by agarose gel electrophoresis. Same gel contained 1 kb and 100 bp DNA ladder as marker. Once the PCR product size was confirmed, the amplified PCR product was cloned onto a PCR cloning vector pTOPO 2.1, which is 3.908 kb in size (FIG. 1).

One μl of PCR reaction mix was mixed with 1 μl of pTOPO 2.1 vector and 4 μl of salt solution composed of 1.2M NaCl and 0.06M $MgCl_2$. The reaction was incubated at room temperature (25° C.) for 5 minutes. The reaction was transferred to an ice bath until it was used to transform competent *E. coli* cells.

*E. coli* TOP10 cells were made competent by the method of Cohen et al., (1972). An overnight culture of *E. coli* TOP10 was diluted 1:1000 in fresh LB medium without any antibiotic and incubated at 37° C. for 3 hours under shaking conditions (200 rpm). Cell density was measured at 600 nm in a spectrophotometer and confirmed to be between 0.4 and 0.6 that corresponds to mid log phase of the growth. The cells (50 ml) were chilled on ice for at least 15 minute and transferred to a pre-chilled centrifuge tube in a pre-chilled rotor. The cells were centrifuged at 2,700×g for 10 minutes and supernatant was discarded. The pellet was re-solubilized in 6 ml of 100 mM pre-chilled $MgCl_2$. The cell suspension was incubated on ice for 45 minutes and re-centrifuged at 2,700×g in a pre-chilled rotor for 10 minutes. The supernatant was discarded and the cells were re-solubilized in 2 ml of pre-chilled 100 mM $CaCl_2$. Competent cells thus prepared were aliquoted in a 100 μl volume in pre-chilled sterile eppendorf tubes.

To 100 μl of competent cells, 6 μl of pTOPO vector with amplified PCR product was added. The cells were incubated on ice for 20 minutes after which the cells were given heat shock treatment by immersing them in a 42° C. water bath for exactly 30 seconds. Cells were returned to the ice immediately and kept for 5 minutes. To the cells 300 μl of pre-warm (at 37° C.) LB medium was added and the cells were incubated at 37° C. for 1 h while shaking at 200 rpm. Cells were spread on LB agar plates containing ampicillin (100 μg/ml), X-gal (40 μl of 20 mg/ml), and IPTG (40 μl of 1M). Plates were incubated at 37° C. for not more than 18 hours and white colonies were selected.

A colony PCR screening was performed using the same set of primers as described above for the confirmation of the successful cloning of the PCR product onto the pTOPO vector. With the addition of 2180 bp hemA/M gene, the recombinant plasmid is 6.088 kb in size and was designated as pTOPO-hemA/M (FIG. 1).

Top10 cells bearing pTOPO-hemA/M were grown in 10 ml of LB medium containing ampicillin for 12 hours at 37° C. under continuous shaking (200 rpm). Plasmid was extracted using standard alkaline lysis method using QIAGEN® kit. Plasmid thus obtained was checked for purity by taking optical density (OD) at 260 nm and 280 nm. The purity of the plasmid was further confirmed by agarose gel electrophoresis.

In pTOPO-hemA/M, the hemA/M is flanked with two EcoRI sites. Thus it was possible to excise the hemA/M from the pTOPO vector by restricting the pTOPO-hemA/M with 10 U of EcoRI for 60 minutes at 37° C. The digest was loaded onto a 1% agarose gel and electrophoresed at 100V for 45 minutes. The presence of the insert of 2180 bp in size was confirmed with the help of 1 kb DNA ladder. hemA/M gene was eluted from the gel using gel elution column. The gene was gel eluted by centrifuging the column at 5000×g for 10 minutes. hemA/M gene thus eluted was subcloned onto a 5.46 kb shuttle vector pARO180.

Shuttle vector pARO180 was digested using 10 U of EcoRI at 37° C. for 60 minutes. EcoRI was heat inactivated by placing the reaction tube in a water bath maintained at 65° C. for 15 minutes. The tube was returned on ice and cooled for 5 minutes. In a different reaction tube was added 1 μl of linearized pARO180 and 5 μl of gel eluted 2180 by hemA/M fragment. To the same tube were added 2 μl of 10X ligation buffer and 1 μl of T4 DNA ligase and the total volume was made up to 20 μl with sterile distilled water. The ligation mix was incubated at 16° C. for 12 hours and the ligation mix was used to transform competent Top10 cells as described above. Transformed Top10 cells were spread on LB agar plates containing ampicillin. The plates were incubated at 37° C. for not more than 18 hours and colonies were selected. Colonies containing hemA/M were screened using colony PCR as described above. Top10 cell containing pARO180-hemA/M (FIG. 2) were grown in LB broth containing ampicillin as described above and plasmid was purified using QIAGEN® kit as described above.

pARO180-hemA/M was digested using 10 U of BstXI enzyme at 55° C. for 60 minutes. BstX1 enzyme was heat inactivated by incubating at 70° C. for 15 minutes. BstX1 digested linearized pARO180-hemA/M was polished using T4 DNA polymerase in the presence of 0.1 mM dNTPs. The reaction was incubated at 11° C. for 20 minutes. T4 DNA polymerase was heat inactivated at 70° C. for 10 minutes. The reaction mix was electrophoresed on a 1% agarose gel and linearized and polished pARO180-hemA/M was gel eluted using Millipore gel elution columns as described above (FIG. 2).

A 1.16 kb kanamycin resistant ($kan^R$) gene was PCR amplified using forward primer KS1 5' TCGAGCTCTAGAAGCTTCAGGGCGCAAGGGCTGCT 3' (Seq. ID No.8) and a reverse primer KR1 5' TCGAGCTCTAGAAGCTTCAGAAGAACTCGTCAAGAAG 3' (Seq. ID No. 9) using standard PCR conditions as described above. PCR product was cloned onto pTOPO PCR cloning vector as described above and $kan^R$ cassette was excised out using EcoRI.

Two μl of pARO 180-hemA/M was added to 10 μl of gel purified polished 1.16 kb $kan^R$ gene in a microfuge tube. To the tube, 2 μl of 10X ligase buffer, 5 μl of distilled water and 1 μl of T4 DNA ligase was added. The reaction was incubated at 16° C. for 12 h.

Figure 2:
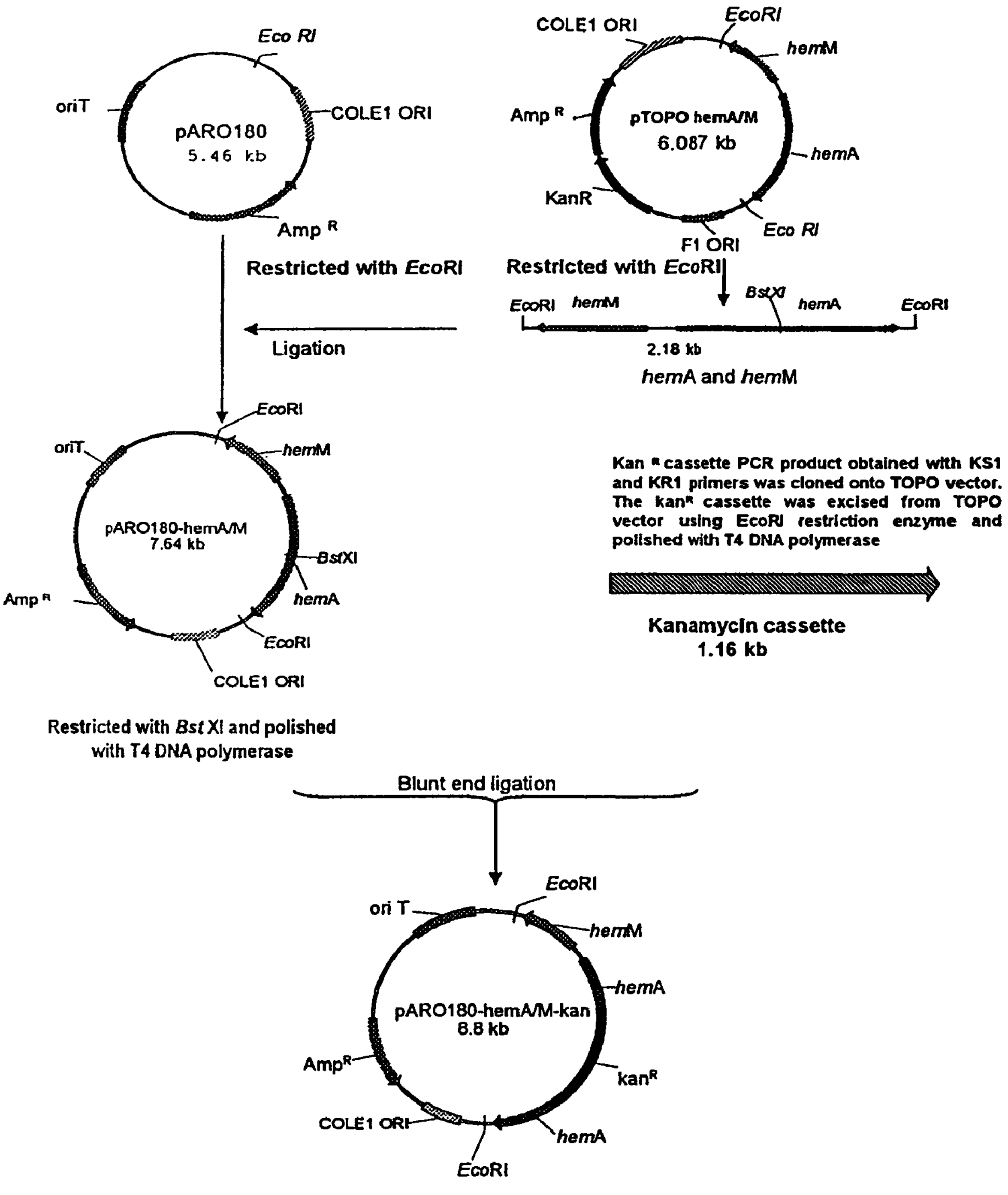

The ligation mix was used to transform competent TOP10 cells. The cells were spread onto LB agar containing ampicillin and kanamycin. Colonies were selected after 18 hours of incubation at 37° C. To confirm the presence of kan $^R$ gene in the hemA gene, two internal primers flanking the kan $^R$ gene, 18R3 5' CTGTTGGTCGGGGCTGGTGAA 3' (Seq. ID No. 6) and VHA-AS4 5' GAGCGACGGGCCTT-TAGTGC 3' (Seq. ID No. 7) were used to perform colony PCR screening. A band of approximately 1.6 kb confirmed the presence of kan $^R$ in the hemA locus. The resultant plasmid was designated as pARO180-hemA/M-kan (FIG. 2). Top10cells containing pARO180-hemA/M-kan were grown and plasmid was purified using QIAGEN® kit.

The hemA gene mutated with kan$^R$ gene was excised by digestion of pARO180-hemA/M-kan with EcoRI. hemA::kan of 3.34 kb was separated from the backbone of pARO180 by electrophoresis and gel eluted using gel elution column (Millipore). Purified hemA::kan fragment was polished using T4 DNA polymerase in the presence of 0.1 mM dNTP as described above.

In order to subclone the hemA::kan onto an oriR6K suicide plasmid, pWM91, the pWM91 was digested using 10 U SmaI enzyme at 37° C. for 60 minutes. SmaI enzyme was heat inactivated at 65° C. for 15 minutes. Two μl of SmaI restricted pWM91 was added to 10 μl of gel purified hemA::kan fragment in a fresh microfuge tube. Blunt end ligation was performed as described above using T4 ligase at 16° C. for 12 hours. The ligation mix was used to transform competent DH5-αλ-pir cells. Colonies were selected on LB agar containing ampicillin and kanamycin after 18 hours. Presence of hemA::kan onto pWM91 was confirmed by colony PCR using 18R3 and VHA-AS4 primers as described above. DH5-λλ-pir cells containing pWM91-hemA/M-kan (FIG. 3) was grown in LB broth containing ampicillin and kanamycin and plasmid was purified using QIAGEN® kit.

Purified pWM91-hemA-kan was used to transform conjugatable λ-pir *E. coli* BW20767. For the replacement of wild type hemA in *V. cholerae O*139 Bengal with mutated hemA, pWM91-hemA-kan was conjugatively transferred to *V. cholerae* O139 Bengal by filter mating. Donor *E. coli* BW20767 ($1\times10^8$ cfu) containing pWM91-hemA-kan were mixed with an equal number of O139 Bengal and thick slurry was dotted on a sterile 0.22 μm nitrocellulose membrane placed on LB agar plate. Donor and recipient cells were allowed to mate for 60 minutes at 37° C. after which the NC membrane was washed in 5 ml of sterile LB broth and plated onto LB agar plates containing ampicillin, polymyxin and kanamycin alone or in combination. Merodiploid was selected from LB agar plate containing ampicillin, polymyxin and kanamycin after overnight incubation at 37° C.

For the curing of the plasmid backbone, the merodiploid were grown in modified LB broth containing no NaCl but containing 15% sucrose and 40 μg/ml ALA overnight at 30° C. Next day, the culture was diluted in modified LB and plated onto modified LB agar i.e. no NaCl but containing 5% sucrose. Plates were incubated at 30° C. for overnight and next day, some 50 colonies were selected and patched on LB agar plates containing 40 μg/ml ALA and with various combinations of antibiotics. Colonies that had lost ampicillin resistance and were not able to grow in the absence of ALA were selected for further analysis as potential mutants.

The VCUSM1 Strain was deposited on Sept. 29, 2003, at the Belgian Coordinated Collections of Microorganisms (BCCM) Laboratorium voor Microbiologie-Bacterienverzameling (LMG), Universiteit Gent. K. L. Ledeganckstraat 35, B-9000 Gent, Belgium under accession number LMG P-22035.

Construction of VCUSM4 Strain

Figure 3:
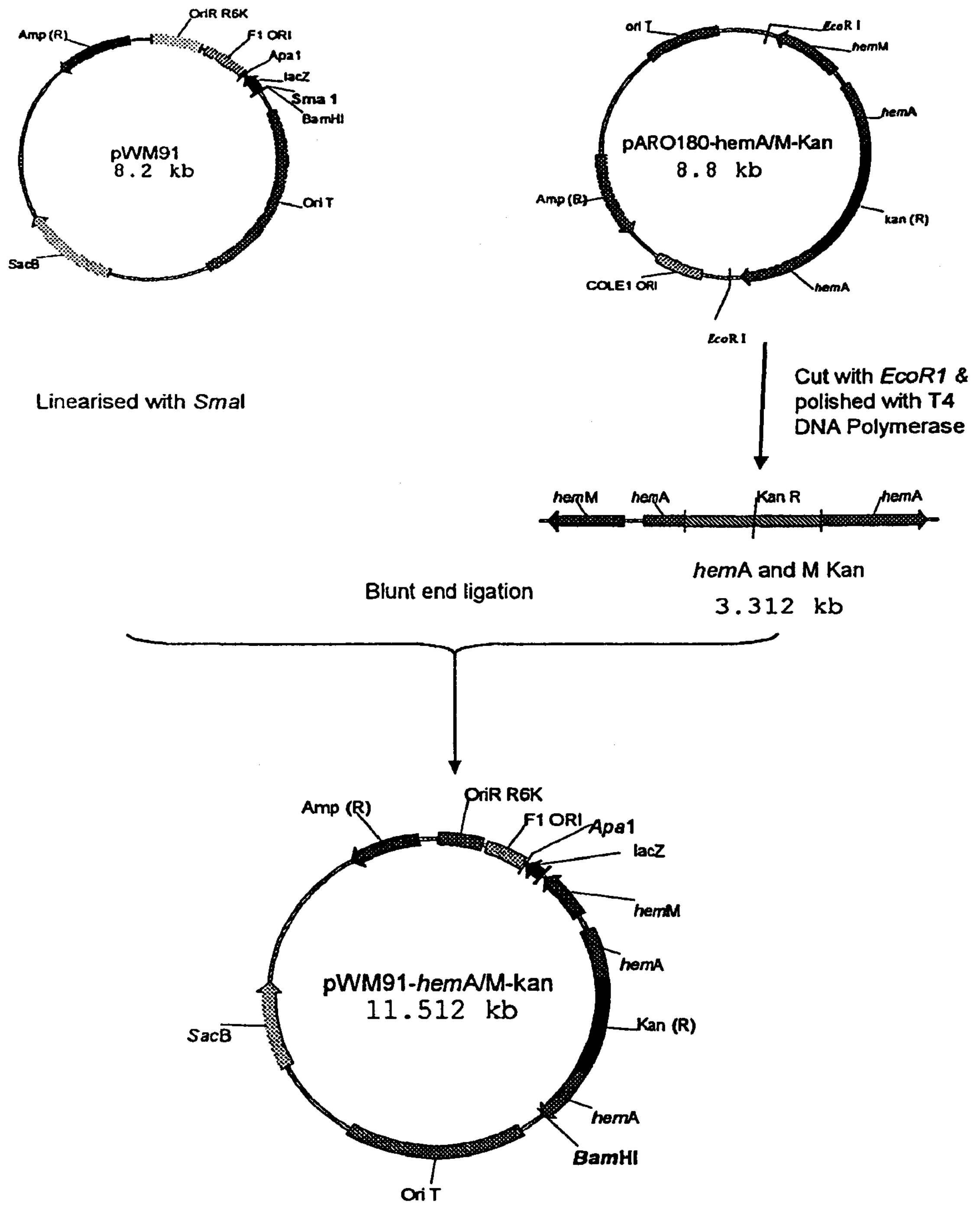

VCUSM4 is an El Tor vaccine candidate developed by mutating its hemA gene by inserting a kan$^R$ cassette essentially as described for VCUSM1 (FIGS. 1, 2 & 3). However, in VCUSM4, kan$^R$ cassette was removed in such a way that a frame shift mutation has taken place within the hemA gene. The resulting mutant cannot synthesize the ALA de novo and depends on an exogenous supply of ALA for its survival.

To develop an ALA auxotroph of El Tor, the methodology is similar as described for O139 Bengal. However, in the last conjugational step, an oriR6K suicidal plasmid carrying a hemA gene mutated with kan$^R$ gene was conjugatively transferred to an El Tor strain to get a hemA::kan mutant.

Next step is to remove kan$^R$ cassette from the hemA gene in such a way that a frame shift mutation occurs. pGFPCR plasmid was used as template to PCR amplify a GFP gene of 968 bp. Two primers GFP-F 5' AGTCATTTAAATGAT-TCATTAATGCAGCTGGC 3' (Seq. ID No. 10) and GFP-R 5' AGTCATTTAAATTTATTTGTAGAGCTCATCCA 3' (Seq. ID No. 11) were designed bearing restriction sites for SmiI enzyme. The above primers were used to amplify the GFP gene. Resultant PCR product of 992 base pairs was confirmed on a 0.8% TAE gel and the PCR amplified GFP was gel eluted using a gel elution column (Millipore). The purified PCR product was polished using T4 DNA polymerase in the presence of 0.1 mM dNTP and stored below −20° C. until use.

Figure 4:
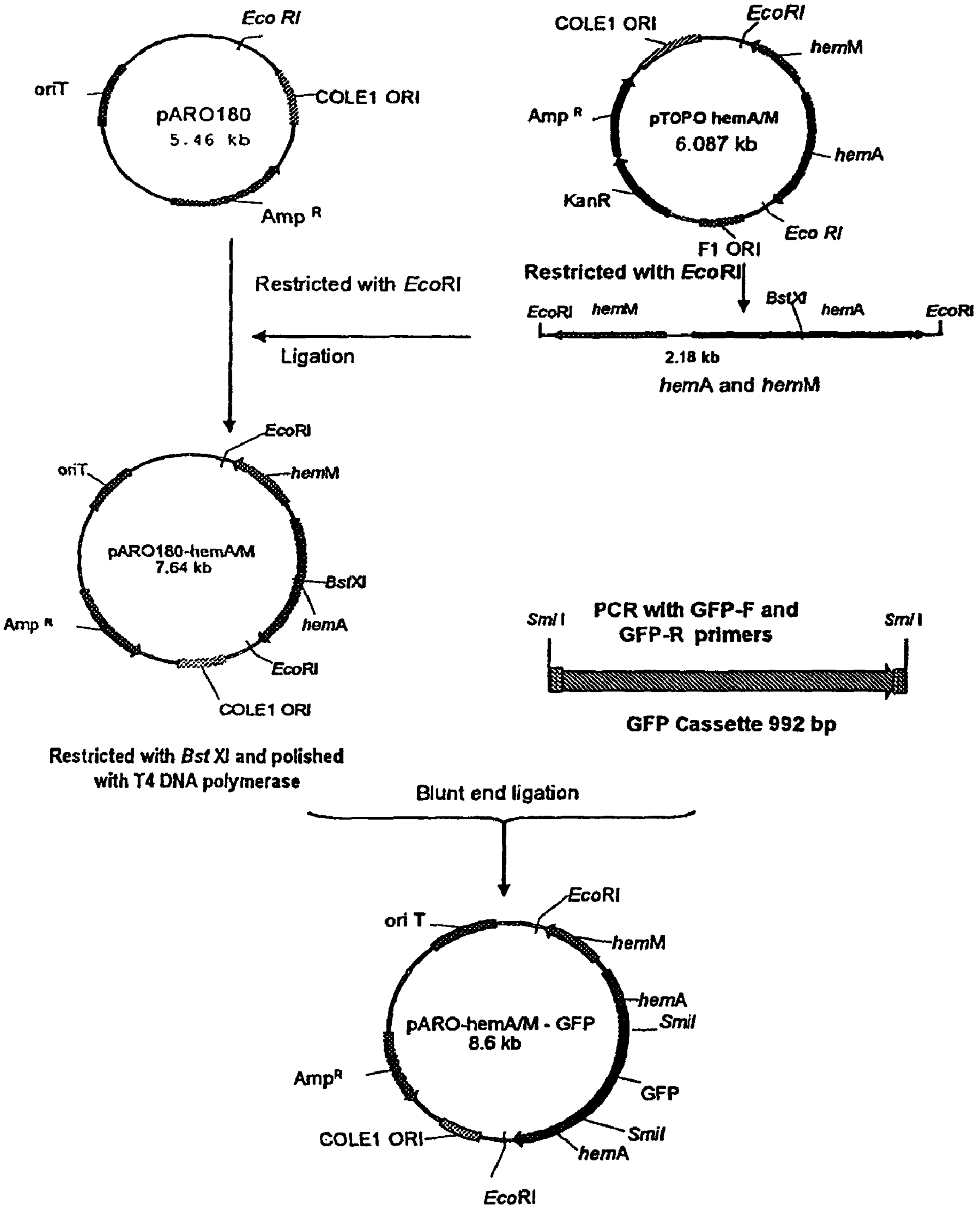

To mutate the hemA gene with GFP, pARO 180-hemA/M vector was digested with BstXI and polished using T4 DNA polymerase in the presence of 0.1 mM dNTP. The linearized vector was analyzed on a TAE gel and purified using gel elution column (Millipore). To the linearized and polished pARO180-hemA/M was added polished GFP cassette in a ratio of 1:10 and incubated in the presence of T4 DNA ligase for overnight for blunt end ligation. The ligation mix was used to transform competent Top10 cells and subsequently plated onto LB agar with ampicillin and incubated for overnight at 37° C. Next day, the plates were observed on a UV (ultra violet) trans-illuminator. Top10 cells harboring pARO 180-hemA/M with a gfp glow in the presence of UV and therefore selected (FIG. 4).

Figure 5:
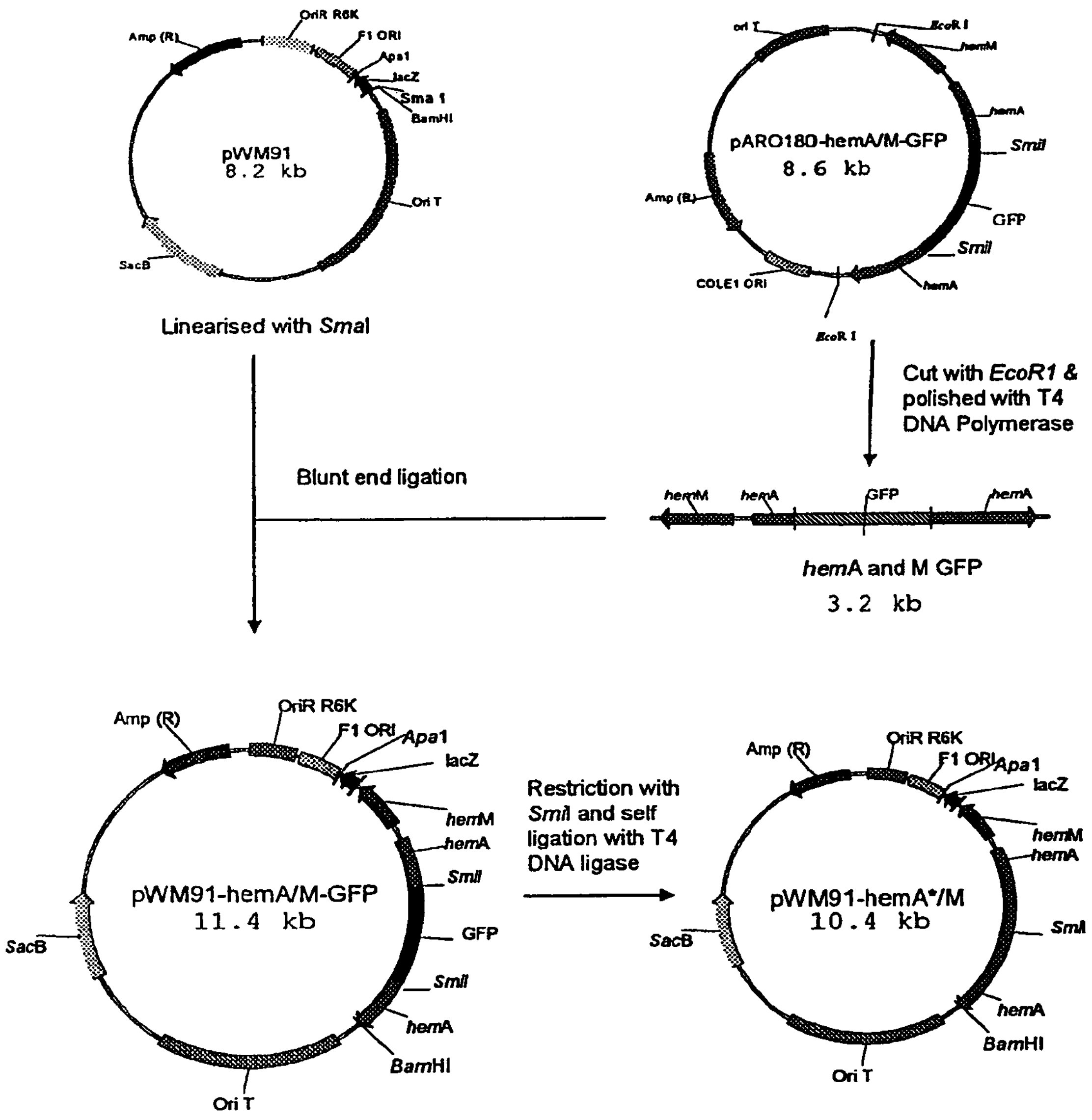

Mutated hemA/M-gfp construct thus obtained was excised out by restricting pARO180-hemA/M-gfp with EcoRI (FIG. 5). hemA/M-gfp is separated from the backbone of pARO180 by electrophoresis and gel eluted using gel elution column (Millipore). Purified hemA/M-gfp was polished using T4 DNA polymerase in the presence of 0.1 mM dNTP as described above.

In order to subclone the mutated hemA/M-gfp onto an oriR6K suicide plasmid, pWM91, the pWM91 was digested using SmaI enzyme and blunt end ligated with the polished hemA/M-gfp using T4 DNA ligase. The ligation mix was used to transform competent DH5-αλ-pir cells. Colonies were selected on LB agar containing ampicillin after 18 hours. Presence of hemA/M-gfp onto pWM91 was confirmed by colony PCR using VHF and VHR primers. DH5-αλ-pir cells containing pWM91-hemA/M-gfp was grown in LB broth containing ampicillin and plasmid was purified using QIAGEN® kit.

In order to create a markerless frameshift mutation in hemA gene, the pWM91-hemA/M-gfp (FIG. 5) was digested with SmiI enzyme. By treating with SmiI enzyme, GFP was excised out from the hemA gene. The filling of sticky ends of BstXI enzyme site in hemA gene with T4DNA polymerase and ligation and excision of GFP gene cassette from Smi I site caused "TGAAAGTCATTTAAATGACT" (SEQ ID NO: 12) sequence insertion at 1415bp position. This has resulted in formation of stop codon at 1435bp position and resulted in mutation of hemA gene. The Smi I digested plasmid pWM91-hemA/M-gfp was electrophoresed to separate it from GFP and subsequently gel eluted using gel elution column. The purified pWM91-hemA/M is self ligated using T4 DNA ligase for overnight and the ligation mix is used to transform competent DH5a cells. Next day, colony PCR screening was performed using 18R3 (Seq. ID No. 6) and VHA-AS4 (Seq. ID No. 7) primers to confirm the loss of GFP from pWM91-hemA/M-gfp.

The pWM91-hemA*/M was transformed onto conjugatable λ-pir *E. coli* host BW20767. For the replacement of hemA::kan with hemA*/M, pWM91-hemA*/M was conjugatively transferred to *V. cholerae* El Tor by filter mating. Donor BW20767 ($1\times10^8$ cfu) containing pWM91-hemA*/M were mixed with equal number of *V. cholerae* El Tor containing hemA::kan and thick slurry was dotted on a sterile 0.22 μm nitrocellulose membrane that has been placed on LB agar plate. Donor and recipient cells were allowed to mate for 60 minutes at 37° C. after which the NC membrane was washed in 5 ml of sterile LB broth and plated onto LB agar plates containing ampicillin, polymyxin, kanamycin and ALA alone or in combination. Merodiploid was selected from LB agar plate containing ampicillin, polymyxin, kanamycin, and ALA after overnight incubation at 37° C.

For the curing of the plasmid backbone, the merodiploid was grown in modified LB broth containing no NaCl but with 15% sucrose and 80 μg/ml ALA overnight at 30° C. Next day, the culture was diluted in modified LB and plated onto modified LB agar i.e. no NaCl but with 15% sucrose. Plates were incubated at 30° C. for overnight and next day, several colonies were selected and patched on LB agar plates containing 80 μg/ml ALA and with various combinations of antibiotics Colonies that had lost ampicillin and kanamycin resistance and were not able to grow in the absence of ALA were selected for further analysis as potential mutants.

The VCUSM4 Strain was deposited on Sept. 29, 2003, at the Belgian Coordinated Collections of Microorganisms (BCCM) Laboratorium voor Microbiologie-Bacterienverzameling (LMG), Universiteit Gent. K. L. Ledeganckstraat 35, B-9000 Gent, Belgium under accession number LMG P-22036.

Materials

DNA modifying enzymes were purchased from New England Biolabs (Beverly, Mass. USA), Boehringer Mannheim Biochemicals (Indianapolis, Ind. USA) and MBI Fermentas (Hanover, Md., USA); enzymes were used according to manufacturer's recommendations. All chemicals and biochemicals were of analytical reagent grade and procured from Sigma Chemical Company (St. Louis, Mo. USA). Bacteriological media was from Oxoid Ltd. (Basingstoke, Hampshire UK). Purified, cholera toxin, cholera toxin B subunit, and AntiRabbit IgG-HRP were from Sigma Chemical Company (St. Louis, Mo. USA). Kits for plasmid purification and PCR purification were from QIAGEN® Inc. (Valencia, Calif. USA). Gel elution column were from Millipore Corp. (Bedford, Mass. USA).

pTOPO TA cloning vector was from INVITROGEN® Corp. (Carlsbad, Calif. USA). pARO 180 was obtained from National Institute of Genetics, Mishima, Japan. pWM91was obtained from University of Maryland. Baltimore, Md. USA. pGFP-PCR was obtained from Dr. Somssich I. of Max Plancks Institut. Koln. Germany.

Bacterial Strains and Culture Conditions

*E. coli* strains Top10, BW20767 and DH5α-λpir were maintained on LB agar without any antibiotics and routinely propagated in LB broth. For selection of clones with various vectors, LB medium was supplemented with ampicillin to a final concentration of 100 μg/ml. Wild type O139 were maintained on LB agar supplemented with polymyxin 0.75 μg/ml. VCUSM1 was maintained on LB agar plates supplemented with polymyxin 0.75 μg/ml, kanamycin 50 μg/ml and ALA 40 μg/ml while VCUSM4 was maintained on LB agar plates supplemented with polymyxin 0.75 μg/ml and ALA 80 μg/ml. Indicator Bengal strains were maintained on Oxoid Nutrient Agar composed of Bacto peptone 10 g/L, Lab lemco powder 10 g/L, NaCl 5 g/L and plain agar 15 g/L supplemented with polymyxin 0.75g/ml. Bacterial strains were routinely propagated at 37° C. in LB or oxoid nutrient broth (ONB) with the appropriate supplements. Thiosulphate citrate bile salt sucrose (TCBS) agar was used to enumerate the VCUSM1 and VCUSM4 in intestinal colonization studies.

Preparation of Bacterial Lysate for PCR

A single colony of O139 Bengal or O1 El Tor was picked up from LB agar plate and diluted into 20 μl sterile water in an eppendorf tube. One drop of sterile mineral oil was added on top of the water to prevent the evaporation. The eppendorf tube was placed in a boiling water bath for 10 minutes. After 10 minutes, the tube was centrifuged at 8000×g for 2 minutes. Clear supernatant was collected and used as DNA template.

Suckling Mouse Model for Intestinal Colonization

The colonization potential of vaccine strains (VCUSM1 and VCUSM4) was evaluated in the suckling mouse cholera model as described by Angelichio in 1999. BALB/c mice, 3-5 days old, were inoculated intra-gastrically with $10^6$ vaccine strain or wild type *vibrio* suspended in 50 μl LB broth. Two independent groups of 8 mice were used for each strain tested. After 16-18 hours, mice were sacrificed by chloroform inhalation and whole gut was recovered aseptically. The gut was homogenized in 5 ml of sterile LB medium with 20% v/v glycerol. Viable cell counts were determined by serial dilution and plating of 10 μl of suspension in triplicate on TCBS plates containing appropriate supplements.

Oral Immunization

Oral immunization of rabbits was carried out as described by Butterton in 1995 with few modifications. Two groups of rabbits, each comprising 4 animals (1-1.5 kg) were immunized with vaccine strain and wild type vibrios respectively on day 0 and 14. Animals were fasted for 24 hours but water was given ad libitum. The animals were sedated with intramuscular ketamine (35 mg/kg) and xylazine (4 mg/kg). After 5 minute, animals were administered intravenously with cimetidine (50 mg/kg) to reduce secretion of acid in the stomach. After 15 and 30 minutes, 15 ml of sterile 5% $NaHCO_3$ was administered intragastrically by the help of a feeding catheter to neutralize the stomach pH which was immediately followed by bacterial inoculum of $10^{10}$ cfu in 15 ml of LB medium. After 30 minutes, 2 ml of morphine (10 mg) was injected intraperitoneally to retard the peristaltic movement. The rabbits were returned to the cages and given limited food and water.

Dose Optimization Studies

In dose optimization study, 4 groups of rabbits comprising of 2 animals/group were immunized with $10^5$-$10^7$ vaccine strain as described above. The fifth group was not immunized and served as control.

Serological Studies

Blood was collected for up to 5 weeks at 1 week intervals from the central auricular artery of immunized rabbits with the help of a 21-gauge needle in sterile vacutainers. Blood was allowed to clot at room temperature for 2 hours to allow the serum to separate. Serum was distributed into 60 μl aliquots in sterile eppendorf tubes and stored below −20° C. without any preservatives until further use.

Anti Cholera Toxin ELISA

Anti-cholera toxin (CT) antibody levels in the immunized and control rabbits were measured by ELISA. Flat bottom 96 well microtiter plates (Maxisorp; NUNC) were coated with 50 ng/well of CT in 50 mM carbonate buffer (pH 9.6) and incubated at 4° C. overnight. Wells were washed 3 times (5 minutes/wash) with wash buffer composed of PBS with 0.05% v/v Tween20 (PBS-T) and blocked with 5% skimmed milk in PBS for 1 hour at 37° C. After washing with PBS-T, 100 μl of rabbit sera of varying dilution (1:10-1:1280 diluted in PBS) was added to the wells and plates were incubated at 37° C. for 2 hours. Plates were washed with PBS-T for 5 times and 100 μl of anti-rabbit IgG or IgA conjugated with HRP (1:5000 in PBS) was added into each well. Plates were incubated at 37° C. for 1 hour and washed with PBS-T for 5 times (5 minutes/wash). 100 μl of freshly prepared ABTS (22'-azino-di[3-ethyl benzthiazoline sulfate]) substrate solution were added to each well and the plates were incubated at 25° C. in the dark for 1-2 hours. Absorbance was recorded at 405 nm with reference to 495 nm using Multiskan EX microtiter plate reader. Titer was calculated as the highest dilution of test serum producing an OD greater than that of the preimmune sera.

Vibriocidal Assay

Vibriocidal antibodies were detected as previously described by Attridge et al. (2002). Indicator strains were grown in ONB for 4-6 hours and diluted with sterile PBS containing 20% pooled normal rabbit serum as complement source to a final concentration of $4\times10^4$ cells/ml. Serum from immunized or unimmunized rabbits was heat inactivated at 56° C. for 30 minutes and diluted in sterile PBS (1:10-1:1280). In 96 well microtiter plate, 50 μl of indicator cells with 20% normal rabbit serum containing complement were mixed with 50 μl of serum from immunized and control rabbits and incubated at 37° C. for 1 hour. After incubation, 50 μl of each cell suspension was plated on TCBS plate and number of viable cells was determined. Titer was calculated as the highest dilution of test serum capable of killing 50% of cells as compared to the preimmune sera.

RITARD Challenge Studies

RITARD (removable intestinal tie-adult rabbit diarrhea) was performed as previously described (Spira et al., 1981) with few modifications. On day 21 of vaccination, the animals were challenged with $10^{11}$ wild type vibrios by RITARD. Briefly, animals were starved for 24 hours and sedated with intramascular ketamine (50 mg/kg), xylazine (8 mg/kg) and acepromazine (1 mg/kg). Hairs on abdomen were shaved and skin was decontaminated with scrub and iodine. A midline incision was made along linea alba and the cecum was brought out to identify the ileocecal junction. The cecum was ligated using sterile 1-O silk suture as close to the ileocecal junction as possible. A reversible knot was tied at the ileum 10 cm away from the ileocecal junction using 1-O catgut. Wild type vibrios ($10^{11}$ in 1 ml of LB medium) were injected into the jejunum 10 cm distal to the stomach using a 25-gauge needle.

The bowel was returned to the cavity and the fascia was closed using 3-O catgut leaving a 1 cm opening in the middle. Skin was also closed in the same way using 3-O silk sutures. After 2 hours, the temporary knot placed in the ileum was removed through the 1 cm opening which was then closed by cat gut and silk sutures. Sterile dressing was applied on the wound and the rabbits were returned to their cages and given limited food and water. A group of unvaccinated (control) animals was challenged in the same way. Animals were monitored for any diarrhea or death every 6 hours for up to 5 days.

Rabbit Ileal Loop Model for Reactogenecity

The Rabbit ileal loop assay was performed as previously described (Thungapathra et al., 1999) with minor modifications. Rabbits were divided in two groups, each comprising of 2 animals (1-1.5 kg). One group was immunized with vaccine strain as described above. Other group left unimmunized and served as control. Animals were anaesthetized and prepared as described above. The abdomen was cleaned as described above and a midline incision was made along linea alba of the abdomen and the small intestine was brought out. The small intestine was ligated 10 cm from the ileocecal junction and was then divided into 12 loops, by ligature using 3-O catgut, of 5 cm each separated by 1 cm segments. Care was taken that no major blood vessel was ligated. The loops were injected with $1\times10^2$-$1\times10^7$ wild type Bengal/El Tor in 0.5 ml LB medium with a 25-guage needle. In another experiment, the loops were inoculated with $1\times10^2$-$1\times10^7$ vaccine strain. The small intestine was returned to the bowel and it was closed by catgut and silk sutures as described above. Sterile dressing was applied on the wound and animals were returned back to their cages. After 18 hours, animals were sedated using ketamine/xylazine as described above followed by the intravenous administration of sodium pentobarbital (50 mg/kg). An autopsy was performed and ligated loops were recovered. Total fluid that was accumulated in each loop and the length of the loop was recorded. Reactogenicity was described as the fluid (ml) accumulated per loop (1 cm) by dividing the length of the loop with volume of the fluid recovered.

Environmental Survival Assays

Environmental survival assay was performed as described by Valle et al., (2000). Water samples (sea, river, tap and sewage) were collected from different places in Kota Bharu Kelantan, Malaysia. Each water sample was aliquoted into three sterile containers containing 10 ml each. The first was left untreated, second was autoclaved at 121° C. for 15 minutes while the third was filter sterilized by passing through 0.22 micron pore size membrane. Vaccine strain and wild type vibrios were grown in LB broth at 37° C. overnight in a shaking incubator. The cells were washed twice with PBS by centrifuging at 2000×g for 15 minutes. Washed cells were adjusted to $1\times10^8$ cells/ml in PBS and 100 μl of this suspension was inoculated in 10 ml of each water sample. Samples were left at room temperature and viability of vaccine strains and wild type vibrios present in the water samples was determined every day by plating an aliquot of 25 μl on each TCBS plate in duplicate for up to 20 days.

REFERENCES CITED

Angelichio, M. J., Spector, J., Waldor, M. K., & Camilli, A. (1999). *Vibrio cholerae* intestinal population dynamics in the suckling mouse model of infection. *Infect. Immun.* 67.3733-3739.

Attridge, S. R., Johansson, C., Trach, D. D., Qadri, F., & Svennerholm, A. M. (2002). Sensitive microplate assay for detection of bactericidal antibodies to *Vibrio cholerae O*139. *Clin. Diagn. LabImmunol.* 9.383-387.

Bondre, V. P., Sinha, V. B., & Srivastava, B. S. (1997). Evaluation of different subcellular fractions of *Vibrio cholerae O*139 in protection to challenge in experimental cholera. *FEMS Immunol. Med. Microbiol.* 19. 323-329.

Butterton, J. R., Beattie, D. T., Gardel, C. L., Carroll, P. A., Hyman, T., Killeen, K. P., Mekalanos, J. J., & Calderwood, S. B. (1995). Heterologous antigen expression in *Vibrio cholerae* vector strains. *Infect. Immun.* 63. 2689-2696.

Cash, R. A., Music, S. I., Libonati, J. P., Schwartz, A. R. & Hornick, R. B. (1974). Live oral cholera vaccine: evaluation of the clinical effectiveness of two strains in humans. *Infect Immun,* 10. 762-4.

Clemens, J. D., Stanton, B. F., Chakraborty, J., Sack, D. A., Khan, M. R., Huda, S., Ahmed, F., Harris, J. R., Yunus, M., & Khan, M. U. (1987). B subunit-whole cell and whole cell-only oral vaccines against cholera: studies on reactogenicity and immunogenicity. *J. Infect. Dis.* 155. 79-85.

Clemens, J. D., Harris, J. R., Sack, D. A., Chakraborty, J., Ahmed, F., Stanton, B. F., Khan, M. U., Kay, B. A., Huda, N., & Khan M. R. (1988). Field trial of oral cholera vaccines in Bangladesh: results of one year of follow-up. *J. Infect. Dis.* 158. 60-69.

Clemens, J. D., Sack, D. A., Chakraborty, J., Rao, M. R., Ahmed, F., Harris, J. R., van Loon, F., Khan, M. R., Yunis, M., & Huda, S. (1990). Field trial of oral cholera vaccines in Bangladesh: evaluation of anti-bacterial and anti-toxic breast-milk immunity in response to ingestion of the vaccines. *Vaccine* 8. 469-472.

Cohen S N, Chang A C & Hsu L (1972). Nonchromosomal antibiotic resistance in bacteria: genetic transformation of *Escherichia coli* by R-factor DNA. Proc Natl Acad Sci 69(8): 2110-4.

Concha, A., Giraldo, A., Castaneda, E., Martinez, M., de la, H. F., Rivas, F., Depetris, A., Svennerholm, A. M., & Sack, D. A. (1995). Safety and immunogenicity of oral killed whole cell recombinant B subunit cholera vaccine in Barranquilla, Colombia. *Bull. Pan Am. Health Organ.* 29. 312-321.

Coster, T. S., Killeen, K. P., Waldor, M. K., Beattie, D. T., Spriggs, D. R., Kenner, J. R., Trofa, A., Sadoff, J. C., Mekalanos, J. J., & Taylor, D. N. (1995). Safety, immunogenicity, and efficacy of live attenuated *Vibrio cholerae O*139 vaccine prototype. *Lancet.* 345. 949-952.

Cooper, S. (2001). Helical growth and the curved shape of *Vibrio cholerae. FEMS Microbiology Letters*. 198. 123-124.

Cryz, S. J., Jr., Kaper, J., Tacket, C., Nataro, J., & Levine, M. M. (1995). *Vibrio cholerae* CVD103-HgR live oral attenuated vaccine: construction, safety, immunogenicity, excretion and non-target effects. *Dev. Biol. Stand.* 84. 237-244.

Dasgupta, U., Bhadra, R. K., Panda, D. K., Deb, A., & Das, J. (1994). Recombinant derivative of a naturally occurring non-toxinogenic *Vibrio cholerae O*1 expressing the B subunit of cholera toxin: a potential oral vaccine strain. *Vaccine.* 12. 359-364.

Faruque, S M., Albert, M. J., & Mekalanos, J. J. (1998). Epidemiology, genetics, and ecology af toxigenic *Vibrio cholerae*. Microbiology and Molecular Biology Reviews. 62 (4). 1301-1314.

Freter R (1962), Detection of coproantibody and its formation after parenteral and oral immunization of human volunteers, *J. Infect. Dis.* 111: 37-48.

Germanier R, Furer E, Varallyay S, & Inderbitzin T M (1976). Preparation of a purified antigenic cholera toxoid. Infect Immun. 13(6):1692-8.

Germanier R, Furer E, Varallyay S, & Inderbitzin T M (1977). Antigenicity of cholera toxoid in humans. J Infect Dis. 135(4):512-6.

Jertbom, M., Svennerholm, A. M., & Holngren, J. (1996). Intestinal and systemic immune responses in humans after oral immunization with a bivalent B subunit-O1/O139 whole cell cholera vaccine. *Vaccine.* 14. 1459-1465.

Kalambaheti, T., Chaisri, U., Srimanote, P., Pongponratn, E., & Chaicumpa, W. (1998). Immunogenicity and protective role of three formulations of oral cholera vaccine. *Vaccine* 16. 201-207.

Kaper, J. B. & Levine, M. M. (1990). Recombinant attenuated *Vibrio cholerae* strains used as live oral vaccines. *Res. Microbiol.* 141. 901-906.

Ledon, T., Valle, E., Valmaseda, T., Cedre, B., Campos, J., Rodriguez, B. L., Marrero, K., Garcia, H., Garcia, L., & Fando, R. (2003). Construction and characterisation of O139 cholera vaccine candidates. *Vaccine.* 21. 1282-1291.

Levine, M. M., Black, R. E., Clements, M. L., Lanata, C., Sears, S., Honda, T., Young C. R., & Finkelstein, R. A. (1984). Evaluation in humans of attenuated *Vibrio cholerae* El Tor Ogawa strain Texas Star-SR as a live oral vaccine. *Infect. Immun.* 43. 515-522.

Levine, M. M. & Kaper, J. B. (1993). Live oral vaccines against cholera: an update. *Vaccine* 11. 207-212.

Levine, M. M. & Noriega, F. (1995). A review of the current status of enteric vaccines. *P.N. G. Med. J.* 38. 325-331.

Mooi, F. R., & Bik, E. M. (1997). The evolution of epidemic *Vibrio cholerae* strains. Trends in Microbiology. 5(4). 161-165.

Nair, G. B., Faruque, S. M., Bhuiyan, N. A., Kamaruzzaman, M., Siddique, A. K., & Sack, D. A. (2002). New variants of *Vibrio cholerae* O1 biotype El Tor with attributes of the classical biotypes from hospitalized patients with acute diarrhea in Bangladesh. *J. Clin. Microbiol.* 40(9). 3296-3299.

Parsi, V. K. (2001). Cholera Prim Care Update Ob Gyns. 8, 106-109.

Pierce, N. F., Kaper, J. B., Mekalanos, J. J., Cray, W. C., Jr., & Richardson, K. (1987). Determinants of the immunogenicity of live virulent and mutant *Vibrio cholerae O*1 in rabbit intestine. *Infect. Immun.* 55. 477-481.

Ryan, E. T. & Calderwood, S. B. (2000). Cholera vaccines. *Clin. Infect. Dis.* 31. 561-565.

Reidl, J., & Klose, K. E. (2002). *Vibrio Cholerae* and cholera: out of water and into the host. FEMS Microbiology Reviews. 26. 125-139.

Sack, D. A., Clemens, J. D., Huda, S., Harris, J. R., Khan, M. R., Chakraborty, J., Yunus, M., Gomes, J., Siddique, O., & Ahmed, F. (1991). Antibody responses after immunization with killed oral cholera vaccines during the 1985 vaccine field trial in Bangladesh. *J. Infect. Dis.* 164. 407-411.

Spira, W. M., Sack, R. B., & Froehlich, J. L. (1981). Simple adult rabbit model for *Vibrio cholerae* and enterotoxigenic *Escherichia coli* diarrhea. *Infect. Immun.* 32. 739-747.

Taylor, D. N., Cardenas, V., Perez, J., Puga, R., & Svennerhohn, A. M. (1999). Safety, immunogenicity, and lot stability of the whole cell/recombinant B subunit (WC/rCTB) cholera vaccine in Peruvian adults and children. *Am. J. Trop. Med. Hyg* 61. 869-873.

Thungapathra, M., Sharma, C., Gupta, N., Ghosh, R. K., Mukhopadhyay, A., Koley, H., Nair, G. B., & Ghosh, A. (1999). Construction of a recombinant live oral vaccine from a non-toxigenic strain of *Vibrio cholerae* O1 serotype inaba biotype El Tor and assessment of its reactogenicity and immunogenicity in the rabbit model. *Immunol. Lett.* 68. 219-227.

Valle, E., Ledon, T., Cedre, B., Campos, J., Valmaseda, T., Rodriguez, B., Garcia, L., Marrero, K., Benitez, J., Rodriguez, S., & Fando, R. (2000). Construction and characterization of a nonproliferative El Tor cholera vaccine candidate derived from strain 638. *Infect. Immun.* 68. 6411-6418.

The invention claimed is:

1. A method of producing a metabolic auxotroph selected from those of *Vibrio cholerae* O139 synonym Bengal and *Vibrio cholerae* O1 El Tor, comprising introducing a mutation into a chromosomal gene according to nucleotide 840 to 2096 of SEQ ID No. 1, which renders said metabolic auxotroph incapable of synthesizing aminolevulinic acid (ALA) de novo.

2. The method according to claim 1, wherein said introducing said mutation comprises inserting a kanamycin resistant gene cassette.

3. The method according to claim 1, wherein said introducing said mutation comprises introducing a frame-shift mutation.

4. The method according to claim 1, wherein said metabolic auxotroph is lyophilized and reconstituted with appropriate buffer for oral consumption.

5. The method according to claim 1, wherein said metabolic auxotroph is obtained from a parent strain originally isolated from a patient's coproculture having all the identifying characteristics of either *Vibrio cholerae* 0139 synonym Bengal or *Vibrio cholerae* O1 El Tor.

6. A method of producing a metabolic auxotroph of *Vibrio cholerae* O139 synonym Bengal, comprising introducing a mutation into a chromosomal gene according to nucleotide 840 to 2096 of SEQ ID No. 1, which renders said metabolic auxotroph incapable of synthesizing aminolevulinic acid (ALA) de novo.

7. The method according to claim 6, wherein said introducing said mutation comprises introducing a frame-shift mutation.

8. The method according to claim 6, wherein said introducing said mutation comprises inserting a kanamycin resistant gene cassette.

9. The method according to claim 8, wherein said metabolic auxotroph is lyophilized and reconstituted with appropriate buffer for oral consumption.

10. The method according to claim 6, wherein said metabolic auxotroph is lyophilized and reconstituted with appropriate buffer for oral consumption.

11. The method according to claim 6, wherein said metabolic auxotroph is obtained from a parent strain originally isolated from a patient's coproculture having all the identifying characteristics of *Vibrio cholerae* 0139 synonym Bengal.

12. A method of producing a metabolic auxotroph of *Vibrio cholerae* O1 El Tor, comprising introducing a mutation into a chromosomal gene according to nucleotide 840 to 2096 of SEQ ID No. 1, which renders said metabolic auxotroph incapable of synthesizing aminolevulinic acid (ALA) de novo.

13. The method according to claim 12, wherein said introducing said mutation comprises inserting a kanamycin resistant gene cassette.

14. The method according to claim 12, wherein said introducing said mutation comprises introducing a frame-shift mutation.

15. The method according to claim 14, wherein said metabolic auxotroph is lyophilized and reconstituted with appropriate buffer for oral consumption.

16. The method according to claim 12, wherein said metabolic auxotroph is lyophilized and reconstituted with appropriate buffer for oral consumption.

17. The method according to claim 12, wherein said metabolic auxotroph is obtained from a parent strain originally isolated from a patient's coproculture having all the identifying characteristics of *Vibrio cholerae* O1 El Tor.

18. The method according to claim 1, wherein said metabolic auxotroph is the strain as deposited under accession number LMG P-22035, and is mutated by inserting a kanamycin resistant gene cassette.

19. The method according to claim 1, wherein said metabolic auxotroph is the strain as deposited under accession number LMG P-22036, and is mutated by introducing a frame-shift mutation.

* * * * *